US010563216B2

(12) United States Patent
Davis et al.

(10) Patent No.: US 10,563,216 B2
(45) Date of Patent: Feb. 18, 2020

(54) COMPOSITIONS AND METHODS OF DELIVERING MOLECULES TO PLANTS

(71) Applicant: Bloomsburg University of Pennsylvania, Bloomsburg, PA (US)

(72) Inventors: George T. Davis, Danville, PA (US); Mark Stocksdale, Bloomsburg, PA (US)

(73) Assignee: Bloomsburg University of Pennsylvania, Bloomsburg, PA (US)

( * ) Notice: Subject to any disclaimer, the term of this patent is extended or adjusted under 35 U.S.C. 154(b) by 81 days.

(21) Appl. No.: 15/488,954

(22) Filed: Apr. 17, 2017

(65) Prior Publication Data

US 2017/0298374 A1    Oct. 19, 2017

Related U.S. Application Data

(60) Provisional application No. 62/324,079, filed on Apr. 18, 2016, provisional application No. 62/432,007, filed on Dec. 9, 2016.

(51) Int. Cl.
   *C12N 15/82* (2006.01)
(52) U.S. Cl.
   CPC ................ *C12N 15/8243* (2013.01)
(58) Field of Classification Search
   None
   See application file for complete search history.

(56) References Cited

U.S. PATENT DOCUMENTS

| 6,462,185 B1 | 10/2002 | Takakura et al. |
| 9,090,517 B2 | 7/2015 | Poo Palam et al. |
| 2004/0139501 A1 | 7/2004 | Hauptmann et al. |
| 2011/0016579 A1* | 1/2011 | Murata ............... C07K 14/415 800/278 |
| 2017/0298374 A1 | 10/2017 | Davis et al. |

FOREIGN PATENT DOCUMENTS

| WO | 9428140 A1 | 12/1994 |
| WO | 9822593 A1 | 5/1998 |
| WO | WO0240688 A2 | 5/2002 |

OTHER PUBLICATIONS

Guo et al (2004, Proc. Natl. Acad. Sci. USA 101: 9205-9210). (Year: 2004).*
Rout et al. ((2009) Effect of Metal Toxicity on Plant Growth and Metabolism: I. Zinc. In: Lichtfouse E., Navarrete M., Debaeke P., Véronique S., Alberola C. (eds) Sustainable Agriculture. Springer, Dordrecht) (Year: 2009).*
Genbank Accession FJ477297, dated Dec. 21, 2008. (Year: 2008).*
UniProt Accession B7UCU7, integrated on Feb. 10, 2009. (Year: 2009).*
Harada et al. (FEBS Letters 581 (2007) 4298-4302). (Year: 2007).*
Bloomsburg University of Pennsylvania, PCT/US2017/027914 filed Apr. 17, 2017, "Notification of Transmittal of the International Search Report and the Written Opinion of the International Searching Authority, or the Declaration", dated Aug. 23, 2017.
Murata, Yoshiko et al., "Transgenic Petunia with the Iron (III)-Phytosiderophore Transporter Gene Acquires Tolerance to Iron Deficiency in Alkaline Environments", Plos One, vol. 10, No. 3, pp. 1-15 Mar. 17, 2015.
Davis, George Thomas et al., A Putative Fe + 3/phytosiderophore (PS) Transporter Isolated from Oats (Avena Sativa), The FASEB Journal, vol. 27, No. 1, Supplement 1017.2 Apr. 2013.
Harada, Emiko et al., "Structural Element Responsible for the Fe(III)-Phytosiderophore Specific Transport by HvYS1 Transporter in Barley", FEBS Letters, vol. 581, pp. 4298-4302 Aug. 13, 2007.
Xiong, Hongchun et al., "Molecular Evidence for Phytosiderophore-Induced Improvement of Iron Nutrition of Peanut Intercropped with Maize in Calcareous Soil", Plant, Cell and Environment vol. 36, (2013) pp. 1888-1902.
Curie, Catherine et al., "Metal Movement Within the Plant: Contribution of Nicotianamine and Yellow Stripe 1-like Transporters", Annals of Botany, vol. 103, pp. 1-11 2009.
Wenrich, Broc et al., "Characterization and Isolation of the Phytosiderophore in Avena Sativa", Abstracts of Papers American Chemical Society, vol. 239, p. 536-CHED Mar. 22, 2010.
Thomson Scientific, London, GB; AN 2002-135373, Japan Sci & Technology Agency Nov. 13, 2001.
Nsoesie, et al., "Synthesis and Optimization of Differentially Protected L-Malic Acid and Avenic Acid Analogs" Poster, 246th ACS National Meeting, Sep. 9, 2013.
Lindsay, et al., "Synthetic Efforts Toward Novel Phytosiderophore Conjugates" Poster, 229th American Chemical Society National Meeting, San Diego, CA, Mar. 13, 2005.
O'Conner, et al., "Synthesis of Fluorescent-Labeled Phytosiderophore Analogs" Poster, 233rd American Chemical Society National Meeting, Chicago, IL, Mar. 25, 2007.
Davis, G. T., et al., "Avena Sativa Iron/Phytosiderophore Transporter mRNA, Complete CDS," GenBank: FJ477297.1, Dec. 21, 2008.

(Continued)

*Primary Examiner* — Charles Logsdon
(74) *Attorney, Agent, or Firm* — McKee, Voorhees & Sease, PLC

(57) ABSTRACT

Compositions and method of delivering a molecule to a plant are provided. In an embodiment, an avenic acid transporter is introduced into a plant. The plant may be a non-graminacious or dicotyledonous plant which does not comprise the transporter in the wild type form. The transporter may be modified to increase uptake of avenic acid along with iron chelated by the avenic acid and/or a molecule conjugated with the avenic acid. Further embodiments provide for conjugating the avenic acid with a molecule for uptake and delivery to the plant. In this manner plant health may be improved by uptake of iron where it would otherwise not occur and/or uptake of the conjugated molecule. The molecule may be a molecule that improves health of the plant. Still further embodiments provide for analogs of avenic acid. Embodiments provide for interplanting *Avena sativa* which natively produces avenic acid with another plant. Additional embodiments provide for time release of avenic acid provided to a plant.

3 Claims, 28 Drawing Sheets
(6 of 28 Drawing Sheet(s) Filed in Color)
Specification includes a Sequence Listing.

(56) References Cited

OTHER PUBLICATIONS

Murata, et al., "A Specific Transporter for Iron(III-phytosiderophore in Barley Roots," The Plant Journal, (2006) vol. 46, pp. 563-572, Jan. 9, 2006.

Schaaf, et al., "ZmYS1 Functions as a Proton-Coupled Symporter for Phytosiderophore- and Nicotianamine-chelated Metals," The Journal of Biological Chemistry, vol. 279, No. 10, pp. 9091-9096, Mar. 5, 2004.

Davis et al., "Compositions and Methods for Delivery of Molecules to Plants", Application for the Pennsylvania State University, U.S. Appl. No. 16/388,462, 125 pages, filed Apr. 18, 2019.

David-Schwartz et al., "The SlFRK4 promoter is active only during late stages of pollen and anther development", Plant Science, vol. 199-200, pp. 61-70, 2013.

De Jaeger et al., "The plantibody approach: expression of antibody genes in plants to modulate plant metabolism or to obtain pathogen resistance", Plant Molecular Biology, vol. 43, pp. 419-428, 2000.

Geng et al., "Expression analysis of four flower-specific promoters of *Brassica* spp. in the heterogeneous host tobacco", African Journal of Biotechnology, vol. 8(20), pp. 5193-5200, Oct. 19, 2009.

Jeon et al., "Intragenic Control of Expression of a Rice MADS Box Gene OsMADS1", Mol. Cells, vol. 26, pp. 474-480, Nov. 30, 2008.

Marschner et al., "Strategies of plants for acquisition of iron", Plant and Soil, vol. 165, pp. 261-274, 1994.

Nain et al., "Cloning of an ovule specific promoter from *Arabidopsis thaliana* and expression of β-glucuronidase", Indian Journal of Experimental Biology, vol. 46, pp. 207-211, Apr. 2008.

Wellmer et al., "Genome-Wide Analysis of Gene Expression during Early *Arabidopsis* Flower Development", PLoS Genetics, vol. 2, Issue 7, 13 pages, Jul. 2006.

Yang et al., "Analysis of rice OsPLD3 and OsPLD4 genes and promoters", abstract only available, www.https://www.ncbi.nlm.nih.gov/pubmed/1859810, 1 page, Mar. 2008.

\* cited by examiner

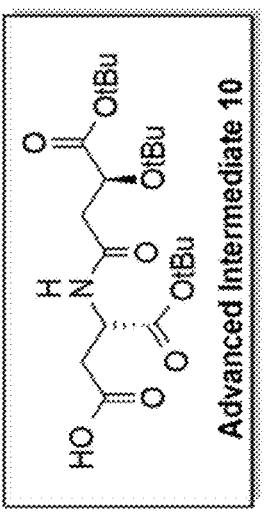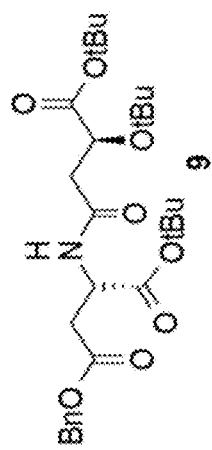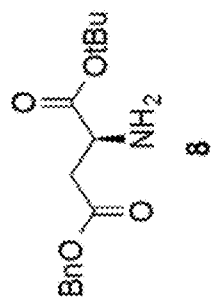
FIG. 8

AvsYS1Sal:

ATGGACGTCCTGGGCCCTGACCGCACGCGGATCGCGCCGGAGATCGAGAAGCACGT
GGCCGCGGAGGGCGACAGGGAGTCTGACCCGGCGCTGGCCGCGGAGCGGGAGCTA
GAGCCCCTGGGGCGGTGGCAGGACGAGCTGACCGTGCGGGGCATGGTGGCGGCGCT
GCTCATCGGGTTCATCTACACCGTCATCGTCATGAAGATCGCGCTCACCACCGGGCT
GGTGCCCACCCTCAACGTCTCCGCCGCGCTGCTCTCCTTCCTCGCGCTCCGCGGCTG
GACGCGCTTGCTGGACCGCTTCGGCATCGTGTCCCGTCCCTTCACGCGGCAGGAGAA
CACCATCGTCCAGACCTGCGGCGTCGCCTGCTACACCATCGCGTTCGCCGGTGGCTT
CGGGTCAACCTTGCTGGGTCTAAACAAGAACACGTACGAGCTGGCCGGCGACTCGC
CGGGCAACGGGCCGGGGAGCTACAAGGAGCCAGGGATTGGCTGGATGACGGCATTC
CTCTTTTCTTGCAGCTTCGGGGGGCTCCTCACCTTGATTCCCCTTAGACAGGTATTGG
TCGTGGACTATAGATTAGTGTACCCAAGTGGG ACGGCAACTGCTGTTCTTATAAACG
GATTTCATACCGCTCAAGGAGACAAGAAC TCCAGGAAGCAAATCCGTGGGTTCTTG
AAGTACTTCGGGGGTAGCTTTTTATGGAGC TTCTTCCAGTGGTTCTACACCGGCGGC
GACGTTTGTGGGTTCATTCAGTTCCCTAC TTTTGGTCTGAAGGCCTGGAAGCAGACG
TTCTTCTTTGACTTTAGCCTGACATACATCGGTGCCGGGATGATCTGCCCACATATAG
TAAATATCTCCACCCTCTTGGGTGCAATTC TTTCTTATGGGATATTG TGGCCACTCAT
CAGTAAGAACAAGGGTGACTGGTACCCT GCAGATGTCAAAGAAAGCAGCATGAAAA
GTTTGTACGGTTACAAGGC CTTCATATGCATCGCTCT GATCATGGGGGATGGACTCT
ACCACTTCACCAAAATTATTACC GTCGACTGCAAGGGCATGTATCGACAG *TTCAGCC
GTAAACATGCTGACAACCGAGAGAAAAATGTGGACAATACAGTC*TCACTCGAGGATTTGC
AGCGCGACGTCGACTTCAAGAGGGGCCATCTCCCCGCTTGGATCGCGTACAGTGGG
TATGCCGTGCTGAGCGTCGT TGCAGTGGTTACCACGCCAATAATGTTCCGACAAGTG
AAATGGTACTACGTAGTTATAGCCTATGTCGTCGCCCCATGCTTGGATTCGCCAAT
TCCTACGGGACGGGGCTCACCGACATCAACATGGGCTATAACTATGGCAAGATAGG
GCTCTTCGTCTTCGCGGGTTGGGCTGGCAGGGACAATGGTGTCGTTGCAGGTCTGGT
TGTTGGTACATGTGTGAAGCAGCTGGTG CTGATATCTGCAGATTTGATGCAAGACTT
CAAGACGAGTTATCTCACTAAGACATCA CCAAGATCCATGATGGTGGCACAGGCAA
TTGGGACAGCCATGGGCTGCGTTGTCTCTCCC TTACGTTCATGCTCTTCTACAGGGC
ATTTGATATTGGCAATCCAGATGGTACCTGGA AGGCACCGTATGCACTGATATACCG
TAATATGGCAATACTCGGTGTGGAGGGC TTCTCAGTACTGCCCAAGTATTGCCTGGC
ACTCTCTGGTGGATTTTTCGCGTTTGCAGCAATCCTCAGCATAGCAAGAGATTTCAC
GCCGCATAGGTATAGGCAGTATGTGCCCCTGCCAATGGCGATGGCGGTTCCATTCCT
TGTCGGCGGGAGCTTTGCGATTGATATGTGTGTCGGGA GTTTGGTGGTTTTTATCTGG
AACAAGATAAACAAGAAGG AGGCCGGCTTCATGGTCCCT GCAGTTGCATCCGGTTT
GATATGTGGGGATGGGATATGGACATTCCCTTCGTCCATACTTGCTCTTGCCAAGAT
TACACCACCAATTTGCAT GAAGTTTACACCTGCACCCTAG

*FIG. 20*

MDVLGPDRTRIAPEIEKHVAAEGDRESDPA LAAERELEPLGRWQDELTVRGMVAALLIG
FIYTVIVMKIALTTGLVPTLNVSAALLSFLAL RGWTRLLDRFGIVSRPFTRQENTIVQTCG
VACYTIAFAGGFGSTLLGLNKNTYELAGDSPG NGPGSYKEPGIGWMTAFLFSCSFGGLL
TLIPLRQVLVVDYRLVYPSGTATAVLINGF HTAQGDKNSRKQIRGFLKYFGGSFLWSFFQ
WFYTGGDVCGFIQFPTFGLKAWKQTFFFD FSLTYIGAGMICPHIVNISTLLGAILSYGILW
PLISKNKGDWYPADVKESSMKSLYGYKAFI CIALIMGDGLYHFTKIITVDCKGMYRQ*FSR*
*KHADNREKNVDNTV*SLEDLQRDVDFKRGHLPAWIAYSG YAVLSVVAVVTTPIMFRQVK
WYYVVIAYVVAPMLGFANSYGTGLTDINM GYNYGKIGLFVFAGWAGRDNGVVAGLV
VGTCVKQLVLISADLMQDFKTSYLTKTSPRSMMVAQAIGTAMGCVVSPLTFMLFYRAF
DIGNPDGTWKAPYALIYRNMAILGVEGFSVLP KYCLALSGGFFAFAAILSIARDFTPHRY
RQYVPLPMAMAVPFLVGGSFAIDMCVGSLVVFIWNKINKKEAGFMVPAVASGLICGDG
IWTFPSSILALAKITPPICMKFTPAP-

*FIG. 21*

MDVLGPDRTRIAPEIEKHVAAEGDRESDPA LAAERELEPLGRWQDELTVRGMVAALLIG
FIYTVIVMKIALTTGLVPTLNVSAALLSFLAL RGWTRLLDRFGIVSRPFTRQENTIVQTCG
VACYTIAFAGGFGSTLLGLNKNTYELAGDSPG NGPGSYKEPGIGWMTAFLFSCSFGGLL
TLIPLRQVLVVDYRLVYPSGTATAVLINGF HTAQGDKNSRKQIRGFLKYFGGSFLWSFFQ
WFYTGGDVCGFIQFPTFGLKAWKQTFFFD FSLTYIGAGMICPHIVNISTLLGAILSYGILW
PLISKNKGDWYPADVKESSMKSLYGYKAFI CIALIMGDGLYHFTKIITVDCKGMYRQFS
RKHADNREKNVDNTVSLEDLQRD*VDCKGMYRQFSRKHADNREKNVDNTVSLEDLQRDVD*
FKRGHLPAWIAYSGYAVLSVVAVVTTPIMFR QVKWYYVVIAYVVAPMLGFANSYGTG
LTDINMGYNYGKIGLFVFAGWAGRDNGVVAGLVVGTCVKQLVLISADLMQDFKTSYL
TKTSPRSMMVAQAIGTAMGCVVSPLTFMLFYRAFDIGNPDGTWKAPYALIYRNMAILG
VEGFSVLPKYCLALSGGFFAFAAILSIARDFTPHRYRQYVPLPMAMAVPFLVGGSFAIDM
CVGSLVVFIWNKINKKEAGFMVPAVASGLICG DGIWTFPSSILALAKITPPICMKFTPAP-

*FIG. 22*

COMPOSITIONS AND METHODS OF DELIVERING MOLECULES TO PLANTS

REFERENCE TO RELATED FILINGS

This application claims the benefit under 35 U.S.C. § 119(e) of previously filed and provisional application U.S. Ser. No. 62/324,079 filed Apr. 18, 2016, and provisional application U.S. Ser. No. 62/432,007 filed Dec. 9, 2016 the contents of each are incorporated herein by reference in its entirety.

GRANT REFERENCE

This invention was made with government support under Grant No. 2007-35318-18350 awarded by the United States Department Agriculture/CSREES. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 11, 2017, is named Davis_PSU 2015-PSSHE-24_SEQ_ST25 and is 27,178 bytes in size.

BACKGROUND OF THE INVENTION

Projections indicate that for yields to keep pace with the expected increase in demand, the application of agrochemicals must be increased with the resultant detrimental impact on the environment, including chemical pollution and aquatic and marine eutrophication. Tilman, David (1999). Global environmental impacts of agricultural expansion: The need for sustainable and efficient practices. *Proceedings of the National Academy of Sciences of the United States of America.* 96(11): 5995-6000.). For example, it is predicted that another three-fold increase in the rate of nitrogen fertilizer application is necessary to sustain the next doubling of global food production (Tilman, 1999). However, it is estimated that current fertilization practices result in less than ½ of the applied nitrogen either being retained in the field or being taken up by the target crop.

Even though it is abundant in the rhizosphere, the bioavailability of iron is limited by its tendency to form insoluble oxyhydroxide polymers, a situation aggravated in alkaline soils, which constitute ~30% of the world's arable soils (Guerinot, 2001). Consequently, iron is the third most rate limiting nutrient under field conditions, next to nitrogen and phosphorus (Guerinot, Mary Lou (2001). Improving rice yields—ironing out the details. *Nature Biotechnology* 19: 417-418.). Iron is vital for normal plant growth and development (Thoiron, S., Pascal, N., and Briat, J-F. (1997). Impact of iron deficiency and iron re-supply during the early stages of vegetative development in maize (*Zea mays*, L.). *Plant Cell and the Environment.* 20: 1051-1060) where it is necessary for functions such as oxygen transport and storage, electron transfer (redox reactions), and nitrogen fixation. Iron deficiencies manifest themselves in leaf yellowing and necrosis, poor growth, and general weakness.

Grasses, including the cereal grains, represent the world's most economically important plants. They provide more than ⅔rds the nutrition in human diets worldwide (Cassman, 1999) and occupy almost 40% of global cropland (Tilman, 1999). In contrast to dicots and non-graminaceous monocots, most grasses have evolved a method of sequestering and transporting iron, designated Strategy II (Marschner, H. and V. Rhomsfeld. (1994) Strategies of plants for the acquisition of iron *Plant and Soil.* 165:261-274), which includes the synthesis and secretion of low molecular weight molecules (phytosiderophores) that chelate iron and move it to the root where the entire complex is taken in through a transmembrane porter.

Like plants, bacteria secrete iron chelating molecules (siderophores). Siderophores and their analogs have tremendous therapeutic potential. One antimicrobial application has involved the attachment of drugs or other biologically relevant molecules to bacterial siderophores, thus providing species-selective conjugates that are actively transported into microbes. Although a number of studies have demonstrated the feasibility of s species-selective siderophore-mediated drug transport in microbial systems, no work has been done with grasses and their corresponding phytosiderophores. If phytosiderophore conjugates are recognized and transported in plants in a manner analogous to bacteria, they would provide a means of targeting effector molecules to a specific plant group or species. Additionally, although the feasibility of heterologous expression of functional phytosiderophore/iron transporter in yeast has been shown (Murata, 2006, cited below), to date no one has demonstrated $PS/Fe^{+3}$ transporter expression in dicotyledonous plants or other non-graminaceous species. Phytosiderophore transporters expressed in leaves or other aerial tissue of engineered plants, both graminaceous and non-graminaceous, would provide a convenient portal through which to deliver a $Fe^{+3}$-phytosiderophore-effector molecule complexes to a target while excluding neighboring competitors, thus reducing application rates and runoff.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 is a graphic showing steps in production of avenic acid.

FIG. 20 is a nucleotide sequence of AvsYS1Sal (SEQ ID NO: 3) with the region for modification in italics (SEQ ID NO: 4).

FIG. 21 is an amino acid sequence of the translation of the sequence of AvsYS1Sal (SEQ ID NO: 5) with the region identified for modification in italics (SEQ ID NO: 6).

FIG. 22 is an amino acid sequence of AvsYS1Con (SEQ ID NO: 8) with the inserted region in italics (SEQ ID NO: 9).

FIGS. 23A-C are graphs showing comparison of transmembrane predictions of AvsYS1 (A); AvsYS1 Sal (B) and AvsYS1Con (C).

FIG. 24 is a graphic showing model predictions of AvsYS1.

FIG. 25 is a graphic showing model predictions of AvsYS1Sal.

FIG. 26 is a graphic showing model predictions of AvsYS1Con.

SUMMARY

Figure 1:
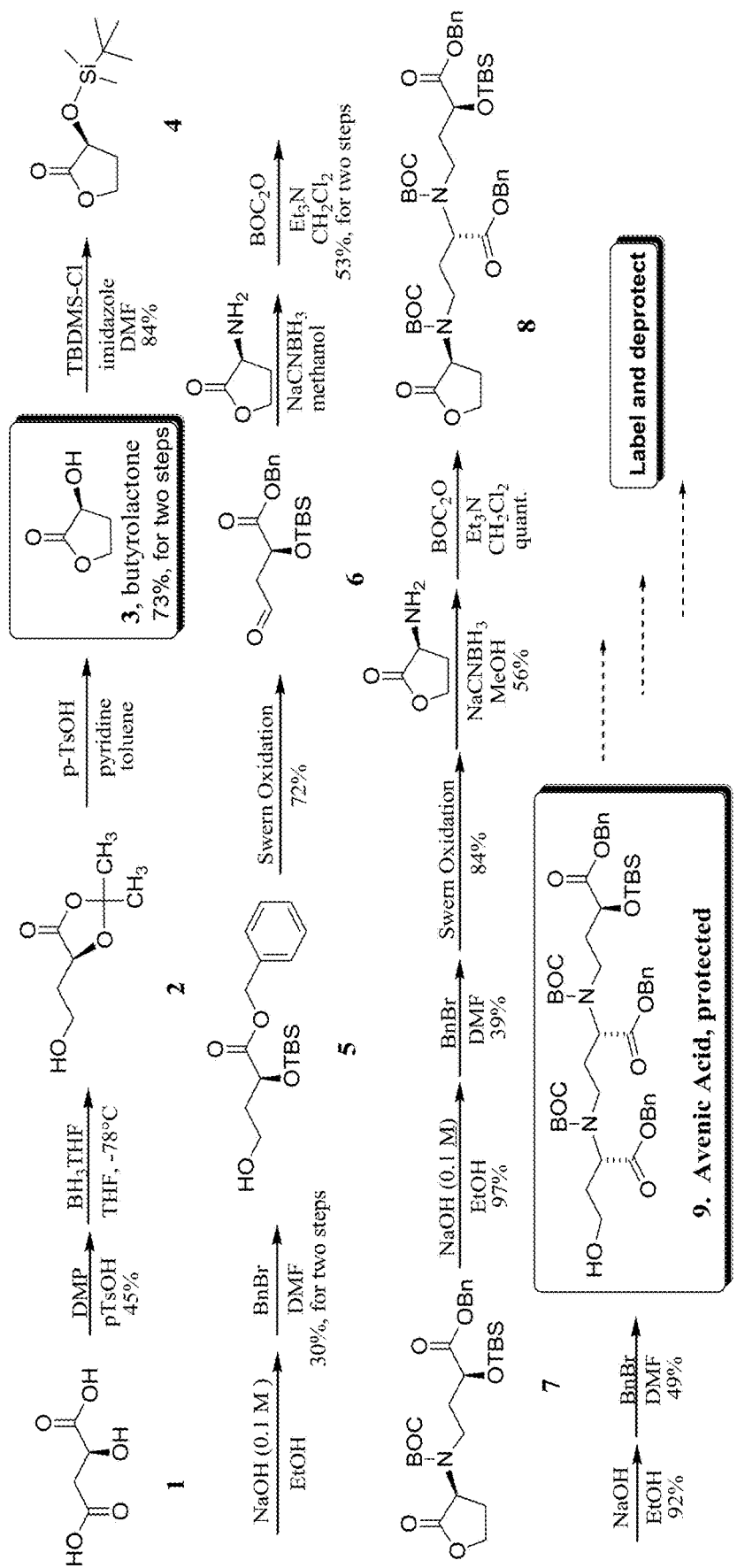
FIG. 1 is a graphic showing synthesis of protected avenic acid.

The methods and compositions here include introducing an avenic acid transporter into a plant. An embodiment provides the plant is one which does not naturally comprise an avenic acid transporter. In one embodiment, the avenic acid transporter is the protein from *Avena sativa* responsible for absorption of avenic acid-iron complex (and engineered avenic acid analogs) from the soil. Plants, such as dicotyledonous plants which otherwise would not benefit from iron delivery by avenic acid uptake may be grown in solids that otherwise would be too alkaline for the plant. The avenic acid transporter may be mutated in still further embodiments. Further, the avenic acid may be conjugated with molecule such that the conjugate delivers the molecule to plant comprising the conjugate. The molecule may be an effector molecule that produces a change in phenotype or genotype of the plant. Additional embodiments provide the molecule improves plant health. An embodiment provides the avenic acid conjugate provides for delivery of the conjugate in selected engineered plants and where plants not comprising the transporter do not benefit from the conjugated nucleic acid molecule. A gene encoding the protein, a vector containing the gene, and a transgenic plant using the vector, as well as methods for uptake of avenic acid engineer constructs by the transgenic plants is provided. Additional embodiments provide for interplanting of *Avena sativa* with other plants to provide a source of avenic acid. In still further embodiments the avenic acid may be provided in a time release controlled formula.

DETAILED DESCRIPTION

Phytosiderophore conjugates provide a means of targeting effector molecules to a specific plant group or species. Phytosiderophore transporters expressed in leaves or other aerial tissue of engineered plants, both graminaceous and non-graminaceous, would provide a convenient portal through which to deliver a $Fe^{+3}$-phytosiderophore-effector molecule complexes to a target while excluding neighboring competitors, thus reducing nitrogen fertilizer application rates and runoff.

Applicants herein provide environmentally friendly alternatives to current practices. Specifically, Applicants present a "Trojan Horse" system to deliver growth effectors with specificity to target plants at the exclusion of non-target plants using the iron uptake system exclusive to grasses. According to the methods here, the system can be used both in grasses which naturally include this uptake system and in other plants that have been engineered to have the same.

The iron-acquisition mechanism of graminaceous plants is comprised of synthesis of avenic acid in the plants, release of the compound into soil, and absorption by the plant of avenic acid-iron complexes formed there. Plants other than graminaceous plants that can actively grow in alkaline soil can be developed provided that the transporter gene that helps absorption of avenic acid-iron complex from soil by the plants is introduced into the plants.

The present methods and compositions comprise the creation of avenic acid conjugates with a molecule of interest, which can be an effector molecule, and for example may be nutrients, growth regulators, herbicides, fertilizers and the like that may be taken up by the graminaceous phtyosiderophore transport mechanism in plants. Specific examples, without intending to be limiting, include: benzene group, oxins, plant hormones (e.g. 2,4-D aka [auxin]), and/or urea. The conjugated nucleic acid molecule can be any nucleic acid molecule desired to be delivered to a plant that does not comprise the nucleic acid molecule, or comprises the nucleic acid molecule in lower amounts than desired. The nucleic acid molecule may be termed an "effector" molecule in the instance where it causes a change in the phenotype or genotype of the plant. In one example, the molecule may deliver a polypeptide that causes the plant growth to increase, delivers nutrients, protects the plant from or makes the plant susceptible to an herbicide, or may change plant biological processes to change plant phenotype such as where an impact of an inhibitor of growth is decreased or eliminated.

The methods and compositions also contemplate uptake not only in grasses which naturally have the avenic acid phytosiderophore but also plants, including dicots which are engineered to include the phytosiderophore transporter. Thus, the invention also includes heterologous expression and function of the avenic acid transporter in dicotyledonous plants or other plants that do not have the avenic acid transport mechanism. Phytosiderophore transporter like proteins have been discovered in *Arabidopsis*, but were unable to transport iron phytosiderophore complexes (Schaaf, G., Ludewig, U., Erenoglu, B. E., Mori, S., Kitahara, G., von Wiren, N. 2004. ZmYS1 functions as a proton-coupled symporter for phytosiderophore- and nicotianamine-chelated metals. (2004). The Journal of Biological Chemistry. 279 (10): 9091-9096).

Because there is species specificity with regard to plant-phytosiderophore interactions, this technology will have application in delivering biologically active molecules such as nutrients, growth regulators, and herbicides to specific targets. Uptake of the conjugate will be limited to the cognate target species and genetically modified transformants, while excluding non-target species and reducing the impact on the environment.

In one aspect of the invention, the invention comprises a nucleic acid encoding a transporter protein for selectively absorbing avenic acid-iron complex; a nucleic acid sequence having at least 90%, 91%, 92%, 93%, 94% homology, more preferably at least 95% homology, or at least 96%, 97%, 98%, or 99% homology thereto or (d) which hybridizes to a nucleic acid sequence which encodes the same under at least moderately stringent conditions.

In one aspect of the invention, the invention comprises proteins or peptides which have the ability to absorb an avenic acid complex as well as modified forms, subsequences or fragments thereof. In one embodiment, it includes a polypeptide comprising (a) a polypeptide comprising at least 90%, 91%, 92%, 93%, 94% homology, more preferably at least 95% homology, or at least 96%, 97%, 98%, or 99% sequence identity to such a polypeptide and (c) a polypeptide comprising said activity and in one embodiment, comprising at least 50 amino acids conserved of (a).

In another aspect, the compositions and methods comprise an expression vector comprising a nucleic acid sequence according to any one of the nucleic acids described above in functional combination with a plant expressible promoter.

In another aspect, compositions and methods comprise a genetically modified plant, plant seed, plant tissue or plant cell transformed with the expression vector described above, wherein the plant, plant seed, plant tissue or plant cell is modified in its ability to uptake avenic acid.

In another aspect compositions and methods comprise a method for producing a genetically modified plant that includes a avenic acid phytosiderophore transporter comprising the steps of: a) introducing into a plant seed, plant tissue or plant cell the expression vector as described above to produce a transformed plant seed, plant tissue or plant cell; and b) regenerating a transgenic plant from the transformed plant seed, transformed plant tissue or transformed plant cell, wherein the modified plant can take up avenic acid compared to a non-modified plant or can take up avenic acid at a level increased compared to a non-modified plant. An embodiment provides the plant can take up avenic acid conjugated to a nucleic acid molecule. In one embodiment, the transgenic plant is a corn or soybean plant. When referring to a wild-type plant, it is meant the plant occurring in nature that has not been modified.

The term introduced in the context of inserting a nucleic acid into a cell, includes transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). Referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) *Breeding Field Crops*. AVI Publication Co., Westport Conn., 4*th* Edit. Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Nucleotide sequences encoding the synthetic proteins disclosed herein can be used in developing other transgenic plants, cells, vectors, antibodies and the like that can be routinely used in breeding programs for incorporating SDS resistance into new soybean cultivars.

In yet another aspect, compositions and methods provide a composition formulated for application to a plant or a part thereof comprising the polypeptide as described. In certain embodiments, the composition is formulated as a spray, a powder, a granule, or a seed treatment. An additional aspect of compositions and methods provide a method for improving the health of a plant, comprising providing to the plant a polypeptide as described herein in an amount that improves the health of the plant as compared to a plant of the same genotype not provided with the polypeptide. An embodiment provides in one instance the polypeptide is avenic acid or an analog thereof. Another embodiment provides the polypeptide comprises a conjugate of avenic acid or an analog thereof and a molecule of interest as described herein. The health of the plant is one or more conditions of the plant and can include functional and/or metabolic efficiency of the plant. Examples, without intending to be limiting, of conditions of the plant that can be improved include growth rate, photosynthesis rate, nutrient uptake, stress reduction, disease resistance, insect resistance, fungal resistance, herbicide resistance, water uptake, reproduction rate, among others.

In certain embodiments, providing the polypeptide comprises contacting the plant with the composition as described, formulated as a spray, a powder, a granule, or a seed treatment or in any other convenient form. In other embodiments, providing the polypeptide comprises expressing in the plant a nucleic acid encoding the polypeptide as described herein.

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "conservatively modified variants" applies to both amino acid and nucleic acid sequences. With respect to nucleic acid sequences, a conservatively modified variant refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)).

The term "nucleic acid construct" or "polynucleotide construct" means a nucleic acid molecule, either single-stranded or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader sequence, polyadenylation sequence, propeptide sequence, promoter sequence, signal peptide sequence, and transcription terminator sequence. At a minimum, the control sequences include a promoter and transcriptional and translational stop signals. The control sequences may be provided with linkers for the purpose of introducing specific restriction sites facilitating ligation of the control sequences with the coding region of the nucleotide sequence encoding a polypeptide.

When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

In the present context, the term "expression" includes any step involved in the production of the polypeptide including, but not limited to, transcription, post-transcriptional modification, translation, post-translational modification, and secretion.

In the present context, the term "expression vector" covers a DNA molecule, linear or circular, that comprises a segment encoding a polypeptide of the invention, and which is operably linked to additional segments that provide for its transcription.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Examples, without intending to be limiting, are provided below.

The term "heterologous" as used herein describes a relationship between two or more elements which indicates that the elements are not normally found in proximity to one another in nature. Thus, for example, a polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g., a genetically engineered coding sequence or an allele from a different ecotype or variety). An example of a heterologous polypeptide is a polypeptide expressed from a recombinant polynucleotide in a transgenic organism. Heterologous polynucleotides and polypeptides are forms of recombinant molecules.

As used herein, the term vector refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, *Proc. Natl. Acad. Sci. U.S.A.* 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, *EMBO J.* 5:3057-3063; U.S. Pat. No. 5,591,439). Examples of non-viral vectors include, but are not limited to, liposomes, polyamine derivatives of DNA, and the like.

The term "host cell", as used herein, includes any cell type which is susceptible to transformation with a nucleic acid construct. By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells.

The term "hybridization complex" includes reference to a duplex nucleic acid structure formed by two single-stranded nucleic acid sequences selectively hybridized with each other.

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" or "polynucleotide" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or cDNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein, a nucleotide segment is referred to as operably linked when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Operably linked elements may be contiguous or non-contiguous. When used to refer to the joining of two protein coding regions, by operably linked it is intended that the coding regions are in the same reading frame. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette can include one or more enhancers in addition to the promoter. By enhancer is intended a cis-acting sequence that increases the utilization of a promoter. Such enhancers can be native to a gene or from a heterologous gene. Further, it is recognized that some promoters can contain one or more enhancers or enhancer-like elements. An example of one such enhancer is the 35S enhancer, which can be a single enhancer, or duplicated. See for example, McPherson et al, U.S. Pat. No. 5,322,938.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". As used herein, the term tissue preferred promoter refers to a nucleic acid sequence that regulates the expression of nucleic acid sequences selectively in the cells or tissues of a tissue of the plant and/or limits the expression of a nucleic acid sequence to the period of tissue formation. Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20.times.SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267-284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acids Probes, Part I, Chapter 2, Ausubel, et al., Eds., Greene Publishing and Wiley-Interscience, New York (1995). In general, a high stringency wash is 2×15 min in 0.5×SSC containing 0.1% SDS at 65° C.

In general, sequences that correspond to the nucleotide sequences described and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

As used herein, "genetically modified plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) The terms "substantial identity" in the context of a peptide indicates that a peptide comprises a sequence with at least 70% sequence identity to a reference sequence, preferably 80%, or preferably 85%, most preferably at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

Identity to the sequence as described would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

The compositions and methods also contemplate uptake not only in grasses which naturally have the avenic acid phytosiderophore but also plants, including dicots which are engineered to include the phytosiderophore transporter.

In one embodiment, the compositions and methods involve the genetic modification of plants to include a phytosiderophore transporter to take up avenic acid conjugates. The transformation of plants and sequences for the same are obtainable by those of skill in the art and using standard techniques as set out below.

When referring to an avenic acid phytosiderophore transporter it is meant a phytosiderophore that can solubilize iron in the soil and take up the resulting iron-phytosiderophore complex and nucleotide sequences encoding the same. Provided below are examples of nucleic acids that encode avenic acid phytosiderophore transporter, the polypeptide of the transporter so encoded. These examples are not intended to be limiting, and any nucleotide sequence encoding avenic acid phytosiderophore transporter, and the transporter so encoded, and conjugates with other molecules is useful in the invention.

Several different phytosiderophores have been isolated and chemically characterized from different grasses and cultivars. In one example, HvYS1 (YS referring to the gene yellow stripe1 (YS1) necessary for uptake of Fe(III)-phytosiderophore) was cloned from barley roots (Murata, 2006). A specific transporter for iron(III)-phytosiderophore in barley roots *Plant J.* 61(1):188). It shows exclusive specificity for the uptake of $Fe^{+3}$ complexed with its cognate phytosiderophore, mugineic acid. Nine analogs have been isolated and identified from graminaceous species and cultivars (Ma (2005). Plant root responses to three abundant soil minerals: silicon, aluminum and iron. *Crit. Rev. Plant Sci.* 24, 267-281). Another example is the maize iron(II)-phytosiderophore transporter, ZmYS1 (Curie et al. (2001). Maize yellow stripe1 encodes a membrane protein directly involved in Fe(III) uptake *Nature* 409, 346-349). *Avena sativa* iron phytosiderophore transporter has also been identified. See Davis et al. (2008) GenBank ACK57536.1 (protein, SEQ ID NO: 1), and GenBank FJ477297 (nucleotide, SEQ ID NO: 2).

We expect bacteria to take up the conjugate (Guerinot, 1994), but the specificity of uptake within grasses is still in question (Murata, 2006). Dicots lack a phytosiderophore-specific transporter, and would thus not be expected to recognize the Fe+3/chelator complex.

Nucleic Acids

The present compositions and methods provide, inter alia, isolated nucleic acids of RNA, DNA, homologs, paralogs and orthologs and/or chimeras thereof, comprising avenic acid phytosiderophore transporter interacting polynucleotides which encode avenic acid phytosiderophore transporter which function in SDS disease development. This includes naturally occurring as well as synthetic variants and homologs of the sequences.

Sequences homologous, i.e., that share significant sequence identity or similarity, to those provided herein derived *Arabidopsis thaliana* or from other plants of choice, are also an aspect of the compositions and methods. Homologous sequences can be derived from any plant including monocots and dicots and in particular agriculturally important plant species, including but not limited to, crops such as soybean, wheat, corn (maize), potato, cotton, rice, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, *papaya*, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassaya, turnip, radish, yam, and sweet potato; and beans. The homologous sequences may also be derived from woody species, such pine, poplar and *eucalyptus*, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. When referring to a homolog it is intended to include orthologs and paralogs. A functional homolog retains the property of being capable of uptake by an avenic acid transporter into the plant. Several different methods are known by those of skill in the art for identifying and defining these functionally homologous sequences. Three general methods for defining orthologs and paralogs are described; a homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) *Nucleic Acids Res.* 22: 4673-4680; Higgins et al. (1996) *Methods Enzymol.* 266: 383-402). Groups of similar genes can also be identified with pair-wise BLAST analysis (Feng and Doolittle (1987) J. Mol. Evol. 25: 351-360).

For example, a clade of very similar MADS domain transcription factors from *Arabidopsis* all share a common function in flowering time (Ratcliffe et al. (2001) *Plant Physiol.* 126: 122-132), and a group of very similar AP2 domain transcription factors from *Arabidopsis* are involved in tolerance of plants to freezing (Gilmour et al. (1998) *Plant J.* 16: 433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in *Bioinformatics: Sequence and Genome Analysis* Cold Spring Harbor Laboratory Press, Cold Spring Harbor, N.Y., page 543).

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) *Nucleic Acids Res.* 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant compositions and methods (for example, transgenic expression of a coding sequence).

Variant Nucleotide Sequences in the Non-Coding Regions

The avenic acid phytosiderophore transporter encoding polynucleotides which function in SDS pathology are used to generate variant nucleotide sequences having the nucleotide sequence of the 5'-untranslated region, 3'-untranslated region, or promoter region that is approximately 70%, 75%, 80%, 85%, 90% and 95% or more, or amounts in-between identical to the original nucleotide sequence of the corresponding SEQ ID NO: 2, 3, 4 or 7, 11, 13, 15, or 17. These variants are then associated with natural variation in the germplasm for component traits related to SDS pathology. The associated variants are used as marker haplotypes to select for the desirable traits.

Variant Amino Acid Sequences of Polypeptides

Variant amino acid sequences of the synthetic polypeptides are generated. Specifically, the open reading frames are reviewed to determine the appropriate amino acid alteration. The selection of the amino acid to change is made by consulting the protein alignment (with the other orthologs and other gene family members from various species). One or more amino acids selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% or more, or amounts in-between are generated using this method. Examples include identifying such variants of SEQ ID NO: 1, 5, 6, 8 and 9. These variants are then associated with natural variation in the germplasm for component traits related to plant growth and cellular elongation. The associated variants are used as marker haplotypes to select for the desirable traits.

The present compositions and methods also includes polynucleotides optimized for expression in different organisms. For example, for expression of the polynucleotide in a maize plant, the sequence can be altered to account for specific codon preferences and to alter GC content as according to Murray, et al, supra.

The avenic acid phytosiderophore transporter interacting polynucleotides comprise isolated polynucleotides which are inclusive of:

(a) a polynucleotide encoding an s polypeptide and conservatively modified and polymorphic variants thereof
(b) a polynucleotide having at least 70% sequence identity with polynucleotides of (a) or (b);
(c) complementary sequences of polynucleotides of (a) or (b).

Construction of Nucleic Acids

The isolated nucleic acids of the present invention can be made using (a) standard recombinant methods, (b) synthetic techniques, or combinations thereof. In some embodiments, the polynucleotides will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide. For example, a hexa-histidine marker sequence provides a convenient means to purify the proteins of the present invention. The nucleic acid—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSGS, pBK, pCR-Script, pET, pSPUTK, p3'SS, pGEM, pSK+/−, pGEX, pSPORTI and II, pOPRSVI CAT, pOPI3 CAT, pXT1, pSGS, pPbac, pMbac, pMClneo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Examples of Synthetic Methods for Constructing Nucleic Acids

The isolated nucleic acids can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides can be modified to alter codon usage. Altered codon usage can be employed to alter translational efficiency and/or to optimize the coding sequence for expression in a desired host or to optimize the codon usage in a heterologous sequence for expression in a particular plant such as maize or soybean. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, a codon usage frequency characteristic of the coding region of at least one of the polynucleotides may be provided. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

An embodiment provides methods for sequence shuffling using polynucleotides and compositions resulting therefrom. Sequence shuffling is described in PCT Publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present methods may further provide recombinant expression cassettes comprising a nucleic acid described here. A nucleic acid sequence coding for the desired polynucleotide of the present invention, for example a cDNA or a genomic sequence encoding a polypeptide long enough to code for an active protein n, can be used to construct a recombinant expression cassette which can be introduced into the desired host cell. A recombinant expression cassette will typically comprise a polynucleotide operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30); and maize H3 histone (Lepetit, et al., (1992) *Mol. Gen. Genet.* 231: 276-85; and Atanassvoa, et al., (1992) *Plant Journal* 2(3): 291-300); ALS promoter, as described in PCT Application No. WO 96/30530; and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may affect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50; and An, et al., (1989) *Plant Cell* 1:115-22); and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are examples of the many options available to a person of skill in the art. See for example, *The Maize Handbook*, Chapter 116, Freeling and Walbot, eds., Springer, New York (1994).

Plant signal sequences may be provided, examples including, but not limited to, signal-peptide encoding DNA/RNA sequences which target proteins to the extracellular matrix of the plant cell (Dratewka-Kos, et al., (1989) *J Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference), or signal peptides which target proteins to the plastids such as that of rapeseed enoyl-Acp reductase (Verwaert, et al., (1994) *Plant Mol. Biol.* 26:189-202) are useful.

The vector comprising the sequences from a polynucleotide of the present invention may comprise a marker gene, which confers a selectable phenotype on plant cells. Usually, the selectable marker gene will encode antibiotic resistance, with suitable genes including gene coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, gene coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), gene coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al. (1987), Meth. Enzymol. 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11, and Berger, et al., (1989) *Proc. Natl. Acad. Sci. USA,* 86:8402-6. Exemplary useful vectors include plasmid pBI101.2 that is available from CLONTECH Laboratories, Inc. (Palo Alto, Calif.).

Expression of Proteins in Host Cells

Using the nucleic acids of the present invention, one may express a protein in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein. To obtain high level expression of a cloned gene, it may be desirable to construct expression vectors which contain, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

One of skill would recognize that modifications could be made to a protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.* 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

The avenic acid phytosiderophore transporter binding gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert avenic acid phytosiderophore transporter binding polynucleotides which function in the plant growth signaling pathway into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., *Science* 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas (1984) *Nature* (London) 311:763-764; Bytebierm, et al., (1987) *Proc. Natl. Acad. Sci. USA* 84:5345-5349 (Liliaceae); De Wet, et al., (1985) In *The Experimental Manipulation of Ovule Tissues*, ed. G. P. Chapman, et al., pp. 197-209. Longman, N Y (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986)*Mol. Gen. Genet.* 202:179-185); all of which are herein incorporated by reference.

Examples of Transformation Options

Methods for introducing expression vectors into plant tissue available to one skilled in the art are varied and will depend on the plant selected. Procedures for transforming a wide variety of plant species are well known and described throughout the literature. (See, for example, Miki and McHugh (2004) *Biotechnol.* 107, 193-232; Klein et al. (1992) *Biotechnology* (N Y) 10, 286-291; and Weising et al. (1988) *Annu. Rev. Genet.* 22, 421-477). For example, the DNA construct may be introduced into the genomic DNA of the plant cell using techniques such as microprojectile-mediated delivery (Klein et al. 1992, supra), electroporation (Fromm et al., 1985 *Proc. Natl. Acad. Sci. USA* 82, 5824-5828), polyethylene glycol (PEG) precipitation (Mathur and Koncz, 1998 *Methods Mol. Biol.* 82, 267-276), direct gene transfer (WO 85/01856 and EP-A-275 069), in vitro protoplast transformation (U.S. Pat. No. 4,684,611), and microinjection of plant cell protoplasts or embryogenic callus (Crossway, A. (1985) *Mol. Gen. Genet.* 202, 179-185). *Agrobacterium* transformation methods of Ishida et al. (1996) and also described in U.S. Pat. No. 5,591,616 are yet another option. Co-cultivation of plant tissue with *Agrobacterium tumefaciens* is a variation, where the DNA constructs are placed into a binary vector system (Ishida et al., 1996 *Nat. Biotechnol.* 14, 745-750). The virulence functions of the *Agrobacterium tumefaciens* host will direct the insertion of the construct into the plant cell DNA when the cell is infected by the bacteria. See, for example, Fraley et al. (1983) *Proc. Natl. Acad. Sci. USA*, 80, 4803-4807. *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) *Plant J.* 6, 271-282 and Lee et al. (1991) *Proc. Nat. Acad. Sci. USA* 88, 6389-6393. Standard methods for transformation of canola are described by Moloney et al. (1989) *Plant Cell Reports* 8, 238-242. Corn transformation is described by Fromm et al. (1990) *Biotechnology* (N Y) 8, 833-839 and Gordon-Kamm et al. (1990) supra. Wheat can be transformed by techniques similar to those used for transforming corn or rice. Sorghum transformation is described by Casas et al. (Casas et al. (1993) Transgenic sorghum plants via microprojectile bombardment. *Proc. Natl. Acad. Sci. USA* 90, 11212-11216) and barley transformation is described by Wan and Lemaux (Wan and Lemaux (1994) Generation of large numbers of independently transformed fertile barley plants. *Plant Physiol.* 104, 37-48). Soybean transformation is described in a number of publications, including U.S. Pat. No. 5,015,580.

*Agrobacterium*-Mediated Transformation

A widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A.* rhizogenes, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species. The selection of either *A. tumefaciens* or *A. rhizogenes* will depend on the plant being transformed thereby. In general *A. tumefaciens* is the preferred organism for transformation.

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene of interest can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505; and Spencer, et al., (1994) *Plant Mol. Biol.* 24:51-61.

Introducing or Increasing the Activity and/or Level of an Avenic Acid Phytosiderophore/$Fe^{+3}$ Transporter Methods are provided to increase the activity (in uptake of avenic acid) and/or level of the avenic acid phytosiderophore transporter to increase or introduce avenic acid/$Fe^{+3}$ uptake. An increase in the level and/or activity of the avenic acid phytosiderophore transporter can be achieved by providing to the plant anaAvenic acid phytosiderophore transporter. The avenic acid phytosiderophore transporter can be provided by introducing the amino acid sequence encoding the avenic acid phytosiderophore transporter into the plant, introducing into the plant a nucleotide sequence encoding an avenic acid phytosiderophore transporter or alternatively by modifying a genomic locus encoding the avenic acid phytosiderophore transporter of the invention.

As discussed elsewhere herein, many methods are known in the art for providing a polypeptide to a plant including, but not limited to, direct introduction of the polypeptide into the plant, introducing into the plant (transiently or stably) a polynucleotide construct encoding a polypeptide having enhanced nitrogen utilization activity. It is also recognized that the methods of the invention may employ a polynucleotide that is not capable of directing, in the transformed plant, the expression of a protein or an RNA. Thus, the level and/or activity of an Avenic acid phytosiderophore transporter may be increased by altering the gene encoding the Avenic acid phytosiderophore transporter or its promoter. See, e.g., Kmiec, U.S. Pat. No. 5,565,350; Zarling, et al., PCT/US93/03868. Therefore, mutagenized plants that carry mutations in Avenic acid phytosiderophore transporter interacting genes, where the mutations increase expression of the Avenic acid phytosiderophore transporter interacting gene or increase the Avenic acid phytosiderophore transporter interacting activity of the encoded Avenic acid phytosiderophore transporter are provided.

Further, it is possible to modify the transporter, such as by mutation. Described below is a method of generating mutant avenic acid transporters and selecting mutants with modifications in a specific loop of the protein.

Avenic Acid Conjugates and Analogs

In one embodiment, a plant may be produced having increased avenic acid uptake by modification of the avenic acid transporter as outlined above. A further embodiment provides a plant not comprising an avenic acid transporter is modified by introducing an avenic acid transporter in order to uptake avenic acid. An avenic acid transporter may also be introduced into a plant already comprising an avenic acid transporter. In a still further embodiment, avenic acid may be conjugated with a molecule of interest and a plant comprising native or introduced or modified avenic acid transporter will take up the conjugate. When referring to a modified transporter it is meant the transporter is changed from the wild type protein, and can be changed by any convenient method, whether chemical or other mutation, synthesis or the like.

Avenic acid conjugates can be synthesized by standard techniques in the art. As discussed supra, the molecule conjugated with avenic acid is a molecule of interest desired to add to the plant via uptake by the avenic acid transporter. The molecule may be any molecule one desires to add, whether for plant health improvement, as discussed supra, or for other purposes. A "conjugate" or "conjugate molecule" or a "conjugate compound" refers to a molecule that comprises two (or more) chemical moieties, which are covalently linked. In specific embodiments, a conjugate or conjugate molecule includes a nucleic acid molecule covalently bound, joined or linked to a moiety of avenic acid. As used herein, "linker", "linking moiety" or "linking group" refer to one or more atoms that connect one chemical moiety to another chemical moiety. The linker may be a molecule in one embodiment comprising at least one atom including carbon, oxygen, sulfur, nitrogen and phosphorus atoms or combinations thereof. According to some embodiments, linkers comprise low molecular weight groups such as amide, ester, carbonate and ether, as well as higher molecular weight linking groups such as alkane-diol based linkers such as butanediol, polyethylene glycol (PEG) based linkers having between 2 and 100 ethylene glycol units, such as for example triethylene glycol units or hexaethylene glycol units, abasic linkers (dSpacers), a peptide, a lipid. As disclosed herein, having a linker refers to a molecule that connects avenic acid to the molecule of interest. In an example, the conjugation may be via ester linkage, amide linkage, ether linkage, or by any other convenient method of linking the molecule with avenic acid. The applicants have found in an embodiment ester linkage allows more effective cleavage and preserves the backbone structure to a higher degree.

For example, conjugation at the terminal amino group is exemplified below with fluorescein:

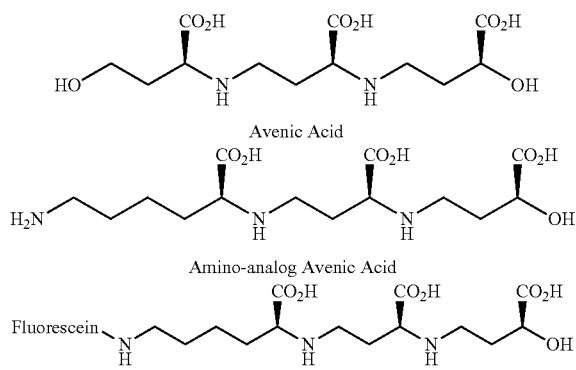

Avenic Acid-Fluorescein Conjugate

Fluorescein is a reporter excited at 493 nm and emitting at 535 nm. It has been used as a vital dye for plant tissues and plant cell cultures (Widholm 1972) and should thus be easily distinguishable from background fluorescence in foot tissues.

Analogs are structural derivatives of a parent compound that in an embodiment differ by a certain component. It may have a substituted atom or compound. Here the analog is a functional analog that retains the ability for uptake by the plant where an avenic acid transporter is present in the plant, and, when conjugated with another molecule, is capable of uptake by the avenic acid transporter. The avenic acid may be modified to provide for improved uptake of the avenic acid and/or avenic acid conjugate. Where so modified, the avenic acid may be conjugated with larger molecules and uptake of the conjugated molecule of interest improved. One example outlined below provides for providing a serine analog with one methylene unit less in the avenic acid primary carbon chain and which can chelate $F^{3+}$. Using a smaller molecule of avenic acid allows for use of such analogs with larger molecules of interest.

Prior work involved precursors in the synthesis of avenic acid and closely related analogs, including (S)-3,4-Di tert-butoxy-4-oxobutonoic acid (See Nsoesie et al. synthesis and optimization of differentially protected L-malic acid and avenic acid analogs Poster, 246th ACS National Meeting Sep. 9, 2013.)

Figure 2:
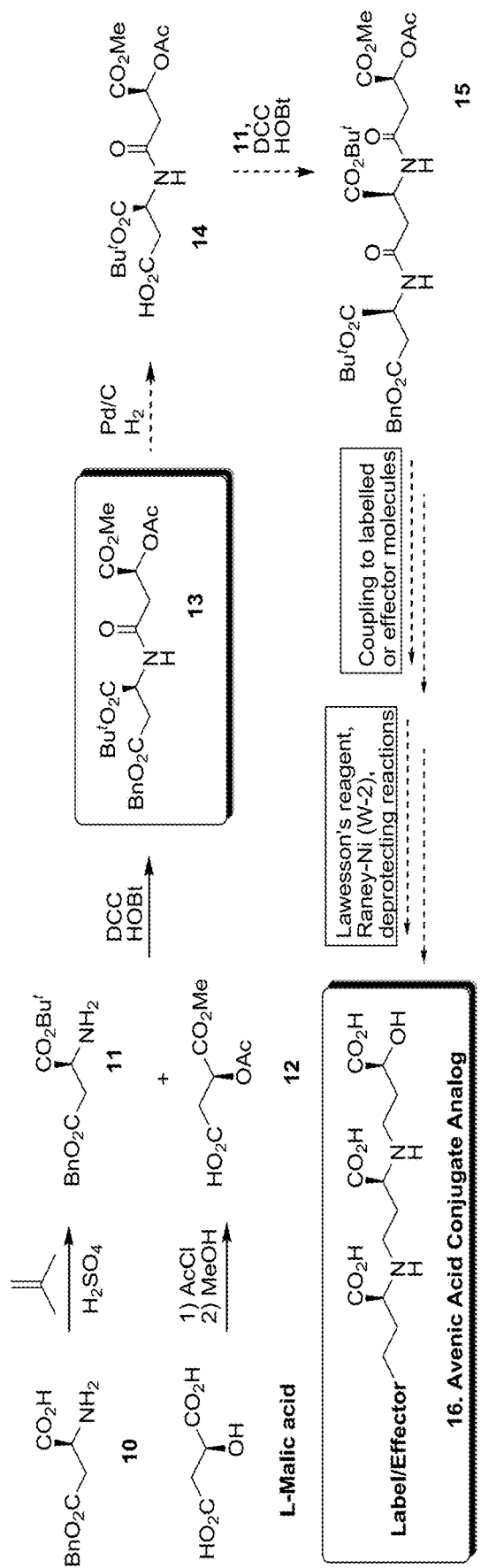
FIG. 2 is a graphic showing a system for synthesis of an avenic acid conjugate analog.

Further work related to the interest in synthesizing novel phytosiderophores such as avenic acid and nicotianamine conjugates and attaching agriculture chemicals. Preparation was carried out using what was referred to as Route A ("Right to Left") or Route B (Thioamide protocol"). The process was as follows. See Lindsay et al. Synthetic efforts toward novel phytosiderophore conjugates, Poster, 229*th* *American Chemical Society National Meeting*, San Diego, Calif., Mar. 13-17, 2005. See FIG. 1 showing Route A. L-malic acid (1) was protected using dimethoxypropane and p-TsOH. The resulting acetonide was reduced to alcohol 2 at −78° C., using anhydrous THF and $BH_3$. Treatment with p-TsOH in toluene resulted in a cyclization and the formation of the commercially expensive hydroxy-butyrolactone 3. The hydroxy group on the butyrolactone was protected using TBDMS-Cl, imidazole and DMF to give protected lactone 4. Lactone 4 was then opened using 0.1N NaOH in EtOH and protected using BnBr in DMF to give alcohol 5. Alcohol 5 then underwent a Swern oxidation to form aldehyde 6 which was then subjected to a reductive amination using amino butyrolactone hydrogen bromide in a solution of 1N $NaCNBH_3$ in methanol at 0° C. Protection of the resulting amine with $(Boc)_2O$ afforded compound 7. In an iterative fashion, compound 7 was extended to give avenic acid precursor 8 and eventually protected avenic acid 9. Compound 9 can now be conjugated to selected labels or effector molecules. See FIG. 2 showing Route B. To complement and possibly expedite the synthesis of desired conjugates, we have also begun to explore the thioamide reduction protocol of Kitahara. Commercially available 10 was further protected as the t-butyl ester using 2-methylpropene at −780° C. L-malic acid was protected via acetylation then methylation to yield 12. DCC/HOBt coupling of 11 and 12 provided amide 13. The treatment of 13 with hydrogen and Pd/C was expected to produce 14. Compound 14 would be coupled to 11 using DCC/HOBt to yield expected peptide 15. Finally, appropriate coupling conditions with selected molecules should yield desired conjugates of avenic acid precursors. Adaptation of the Kitahara thioamide reduction (Lawesson's reagent followed by treatment with Raney-Ni) and then appropriate deprotections should provide final conjugates 16. Additionally, we were able to successfully conjugate anthracene carboxylic acid to alcohol 5.

Figure 3:
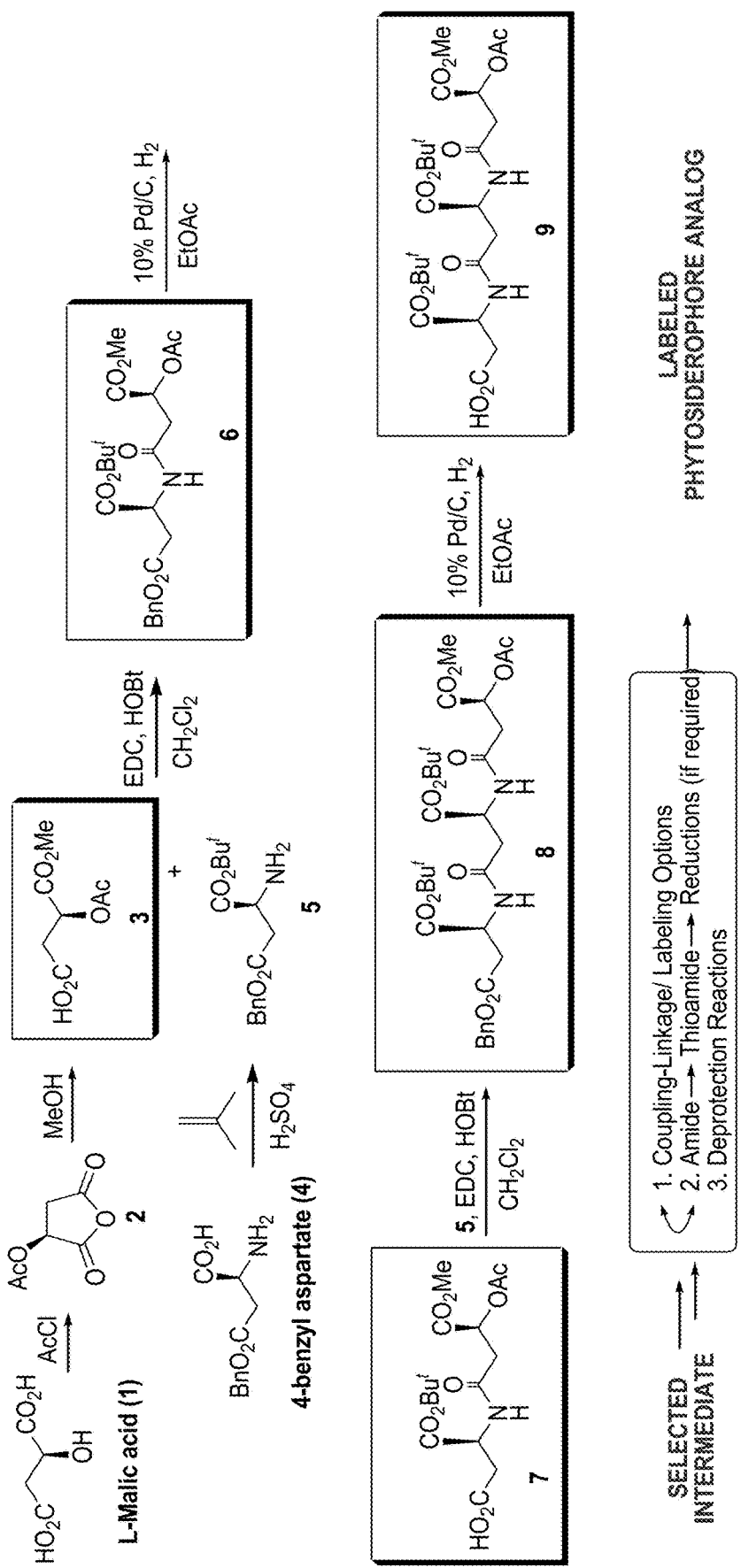
FIG. 3 is a graphic showing steps in production of avenic acid.
Figure 4:
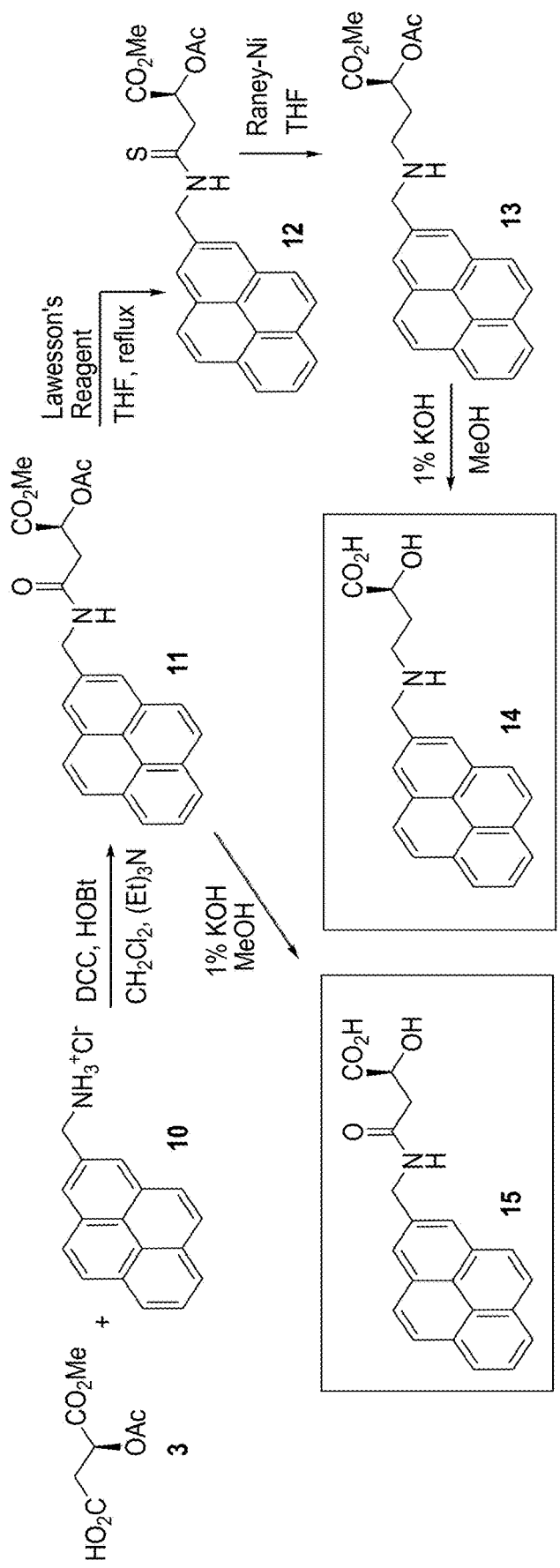
FIG. 4 is a graphic showing steps in production of avenic acid.
Figure 5:
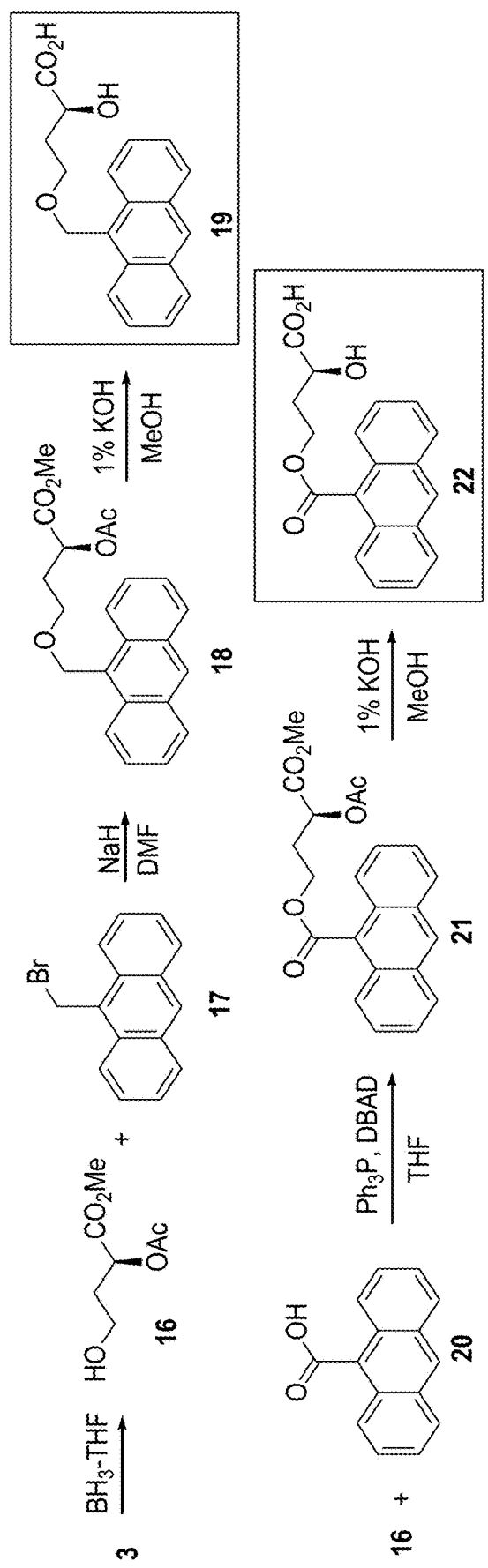
FIG. 5 is a graphic showing steps in production of avenic acid.
Figure 6:
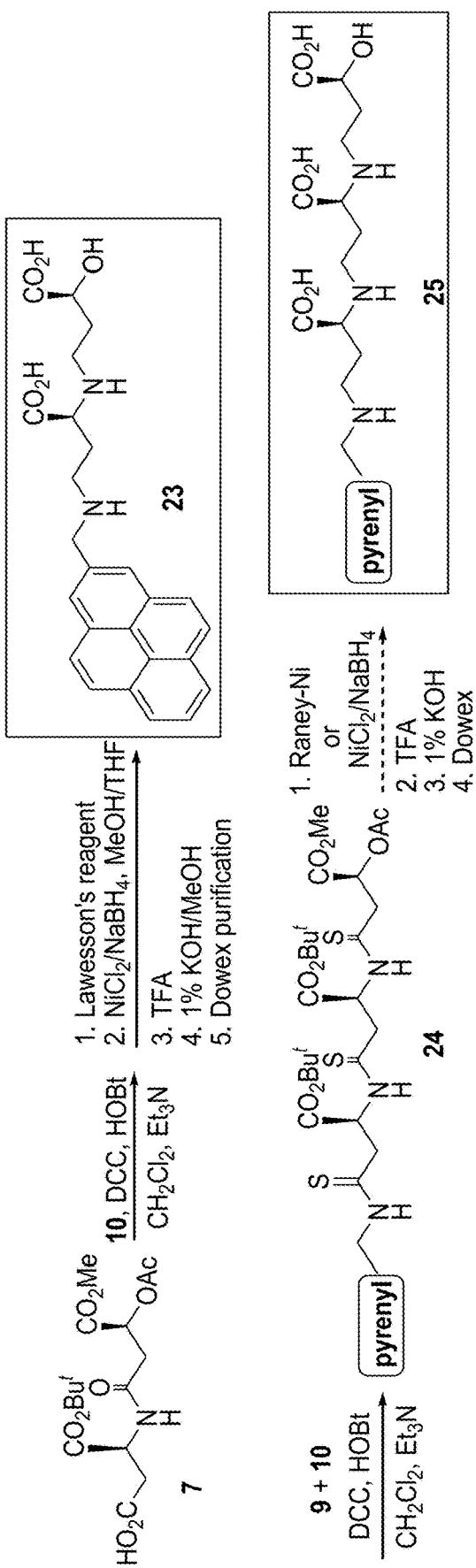
FIG. 6 is a graphic showing steps in production of avenic acid.

Additional work involved what we referred to as Scheme 1, 2 3 or 4, outlined below. Conner et al. Synthesis of fluorescent-labeled phytosiderophore analogs, Poster, 233*rd American Chemical Society National Meeting*, Chicago, Ill., Mar. 25-29, 2007. In Scheme I (see FIG. 3) L-malic acid (1) was selectively protected via treatment with acetyl chloride followed by methanol to yield 3. Commercially available 4 was further protected as the t-butyl ester 5 using 2-methylpropene. EDC or DCC/HOBt coupling of 5 and 3 provided amide 6. Treatment of 6 with hydrogen and Pd/C afforded 7 which was coupled with 5 using EDC or DCC/HOBt to yield polyamide 8 which contains the full carbon backbone of avenic acid. Compound 8 was then treated with hydrogen and Pd/C to yield carboxylic acid 9. Depending on the selected intermediate and chemical label, each highlighted intermediate has been or will be: 1) coupled to the label; 2) converted to the thioamide and reduced (steps 1 and 2 can be switched as needed); and 3) deprotected to prepare a variety of labeled phytosiderophore analogs appropriate for biological study. Shown in FIG. 4 is Scheme 2, where amino pyrene 10 was coupled to 3 to yield fluorescently labeled 11. Conjugate 11 was then treated with Lawesson's reagent to afford thioamide 12 which was further reduced to give protected amine 13. Final removal of protecting groups afforded labeled hydroxy amino acid 14. Alternatively, 11 was directly deprotected to provide amide 15. See FIG. 5, where ether and ester linked conjugates wee explored (Scheme 3), and carboxylic acid 3 was treated with $BH_3$-THF to yield alcohol 16. Treatment of 16 with NaH followed by bromide 17 provided fluorescently labeled, ether-linked conjugate 18. Removal of the protecting groups with KOH/MeOH afforded labeled model compound 19. Alcohol 16 was also coupled to anthracene carboxylic acid 20 via Mitsunobu conditions. Deprotection gave ester 22. FIG. 6 shows Scheme 4 where Acid 7 was coupled to 10 using DCC/HOBT. Lawesson's reagent afforded the thioamide which was reduced by treatment with $NiCl_2/NaBH_4$ (in situ nickel boride) in MeOH/THF. Deprotection and Dowex purification gave labeled analog 23. Likewise, a labeled avenic acid analog (complete backbone and all chelating groups) is underway. Coupling of 9 with 10 followed by treatment with Lawesson's reagent gave thioamide 24. Eventual reduction and deprotection should afford 25.

Figure 7:
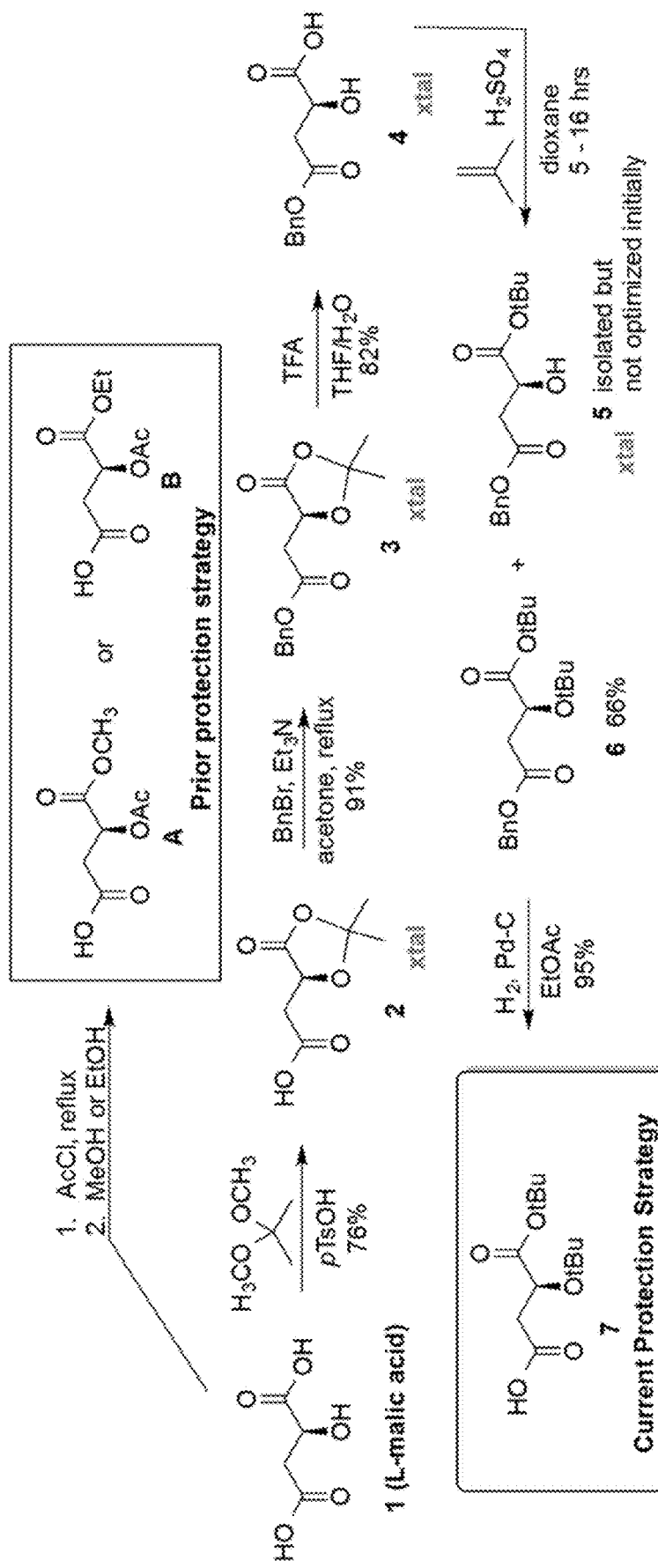
FIG. 7 is a graphic showing steps in production of avenic acid.

Synthesis of avenic acid and analogs investigated further schemes which expanded on earlier schemes as shown below. Nsoesie et al. Synthesis and optimization of differentially protected L-malic adi and avenic acid analogs, 246*th American Chemical Society National Meeting*, Indianapolis, Ind., Sep. 8-12, 2013. This modified scheme is shown in FIG. 7 in Scheme 1. The synthesis of 7 is shown in Scheme 1. L-malic acid (1) was selectively protected as acetonide 2. Treatment of 2 with benzyl bromide afforded benzyl ester 3 which was treated with TFA to produce ester 4. Ester 4 was then reacted with isobutylene and $H_2SO_4$ in dioxane to yield mono-tert-butyl ester 5 and di-tert-butyl ester 6. Finally, hydrogenation of 6 with Pd—C afforded desired differentially protected 7. Intermediates 2, 3, 4, and 5 were also isolable as crystals (labeled as "xtal" in Scheme 1).

Figure 9:
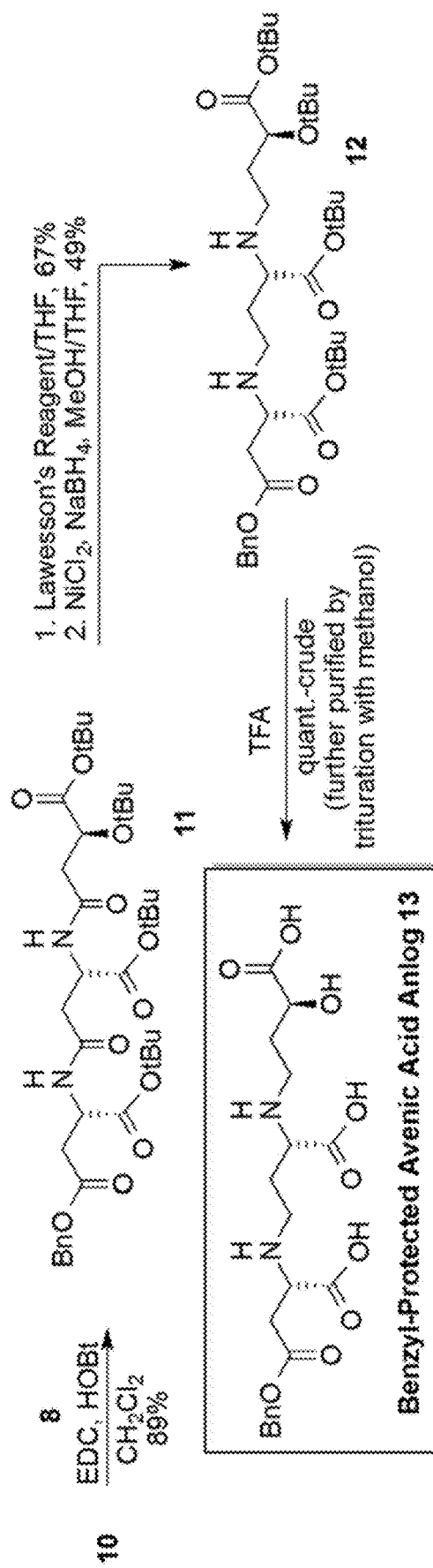
FIG. 9 is a graphic showing steps in production of avenic acid.
Figure 10:
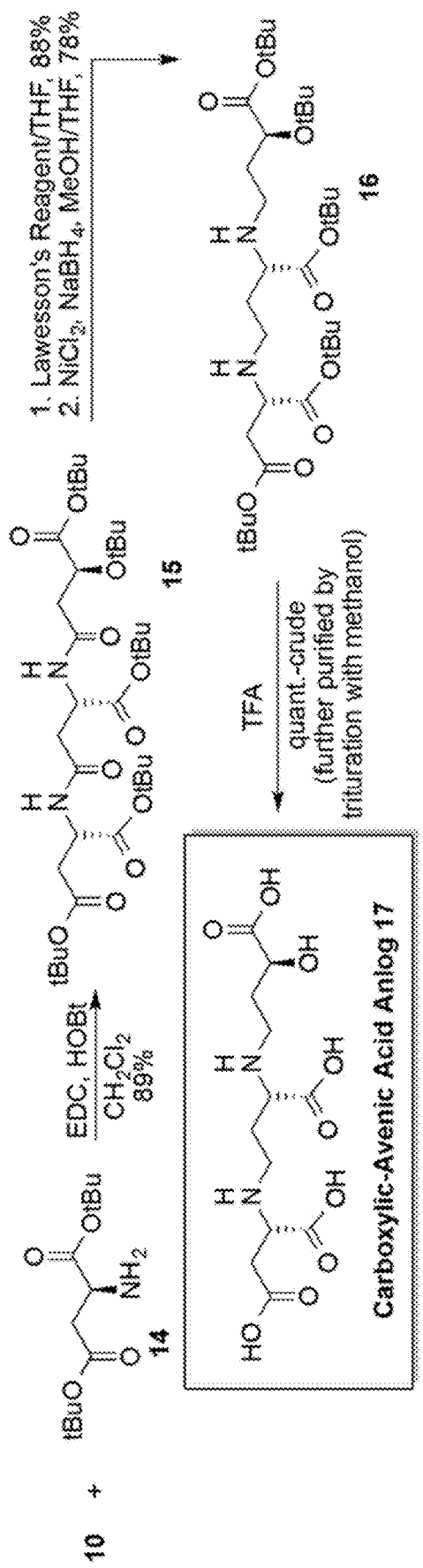
FIG. 10 is a graphic showing steps in production of avenic acid.
Figure 11:
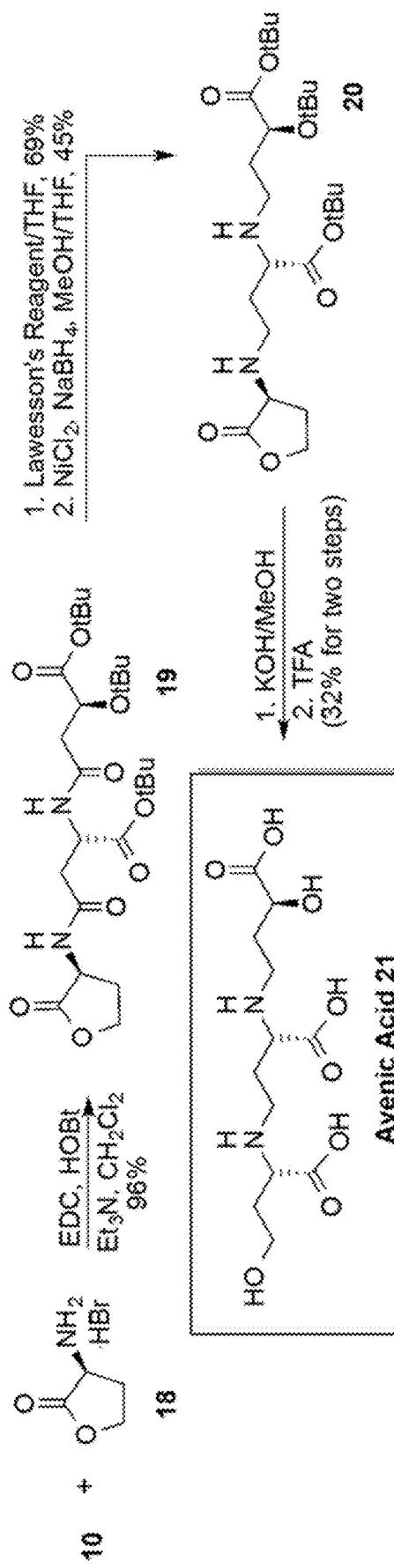
FIG. 11 is a graphic showing steps in production of avenic acid.

In Scheme 2 (FIG. 8) EDC/HOBt coupling of 7 with 8 (previously synthesized in our group) provided amide 9 which was then treated with hydrogen and Pd/C to afford advanced intermediate 10 in good yield and in gram quantities (Scheme 2). Selection of the next protected amino acid (or pro-amino acid) for coupling to intermediate 10 determined the final target phytosiderophore. This approach allowed completion of the synthesis of the three compounds described below. Synthesis of the advanced intermediate is shown in FIG. 9 and Scheme 3. Intermediate 10 was next coupled to 8 to yield polyamide 11. Polyamide 11 was then treated with Lawesson's Reagent (to form the thioamide) followed by reduction with $NiCl_2/NaBH_4$ (in situ nickel boride) to give the fully protected avenic acid analog 12. Treatment of 12 with neat TFA removed the t-butyl groups affording benzyl-protected carboxylic avenic acid analog 13. As shown in FIG. 10, carboxylic avenic acid analog 17 was prepared in analogous fashion utilizing protected aspartic acid 14 (also previously synthesized by our group) in place of 8. TFA treatment of 16 resulted in carboxylic avenic acid analog 17 (Scheme 4). Finally, avenic acid (21) was prepared by first coupling commercially available 18 with advanced intermediate 10 to yield polyamide 19. Conversion to the thioamide followed by reduction afforded "pro" avenic acid 20. The lactone ring was then opened with 0.2 M KOH/MeOH followed by treatment with neat THF to provide avenic acid 21 (Scheme 5, FIG. 11).

Companion Planting

An embodiment provides that avenic acid can be provided to a plant having a native avenic acid transporter, or a plant that does not comprise an avenic acid transporter in the wild type condition but has introduced into it an avenic acid transporter, by planting at least one second plant which produces avenic acid. In one embodiment, the plant is *Avena sativa*. This allows for uptake of $Fe^{3+}$ where it otherwise would not occur, or increases iron uptake where such companion plant is not interplanted or intercropped. The companion plant is planted adjacent to the plant comprising the avenic acid transporter such that the avenic acid may be taken up by the plant comprising the avenic acid transporter. Examples, without intending to be limiting of interplanting or intercropping include planting the at least one plant comprising the native or introduced avenic acid transporter adjacent at least one second plant such as *Avena sativa* by sowing without rows, mixing the plants and sowing together, by first sowing the plant comprising the avenic acid transporter and then sowing the avenic acid producing plant or vice versa, planting adjacent rows of the avenic acid transporter and the avenic acid producing plant. It is to be understood that these are examples and any means of interplanting that allows the plant comprising the avenic acid transporter to uptake the avenic acid produced by the second plant is useful.

Controlled Release of Avenic Acid

Embodiments provide for exposing a plant that natively comprises an avenic acid transporter or into which an avenic acid transporter is introduced to avenic acid that is released over time. Examples of methods of controlling release over time of avenic acid includes coating with a polymer which breaks down over time and/or at a certain temperature. Such polymers may, for example, be thermoplastic resins such as polyvinyl chloride, polyolefin and copolymers; polymeric resin; polyurethane; polysaccharides coatings. Examples include a waterproofing sulfurated coating. Controlled release fertilizers have been produced using a wide range of compounds (See, e.g., U.S. Pat. No. 9,090,517). Here avenic acid is produced in a form that can be released over time. This will allow, for example, planting of soybeans in geographic areas where alkalinity of soil would otherwise result in iron deficiency in plants.

In one embodiment of the invention, a time release structure is created by using tertiary butyl esters. This can be attached by an ester linkage to one or more of the carboxyl groups and/or to one or two of the hydroxyls. An embodiment provides for attachment via an ester linkage to one, two or three of the carboxyls. The result would be different degrees of hydrophobicity and would liberate free avenic acid in stages. One embodiment provides a pelleted form of this formula which would release a non-butylated form, one butylated, two butylated and three butylated form. Such a time release structure can be provided with avenic acid, avenic acid analogs and conjugates.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

Example 1

Preparation of Analogs and Conjugates
Synthesis of Avenic Acid and a Serine-Based Analog of Avenic Acid.

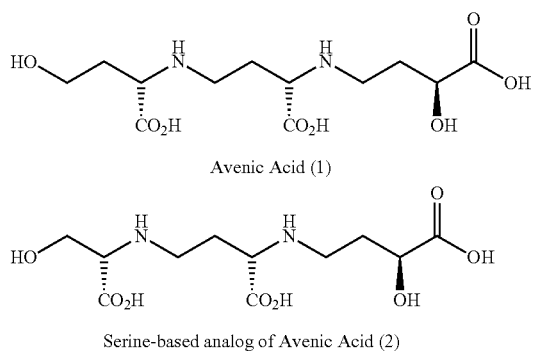

Figure 12:
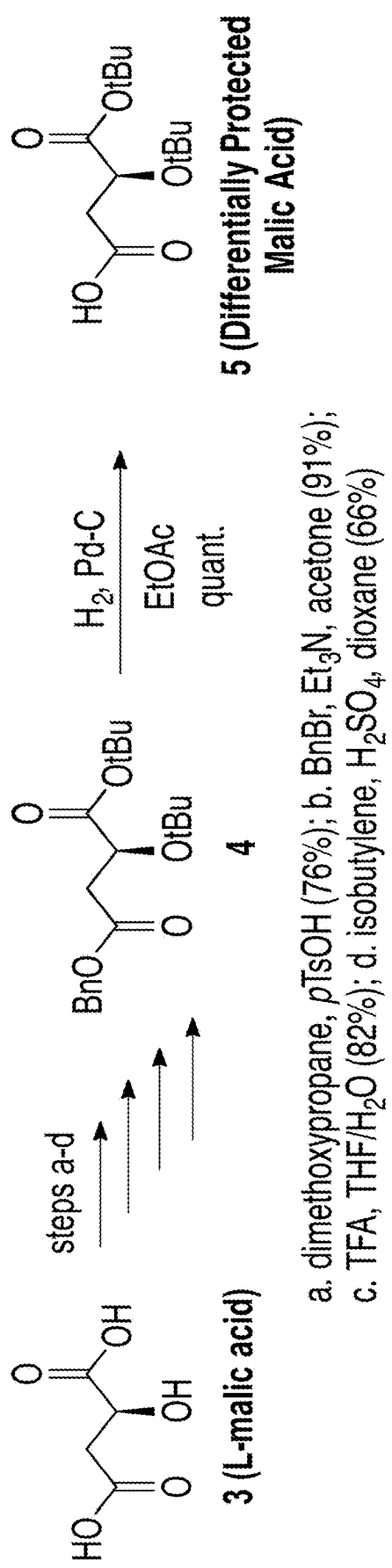
FIG. 12 is a graphic showing steps in production of avenic acid.

The total synthesis of either Avenic Acid (1) or the serine-based analog (2) which is simply one methylene unit shorter began with the preparation of differentially protected L-malic acid 5 in five good yielding steps beginning with commercially available L-malic acid 3. See FIG. 12.

Figure 13:
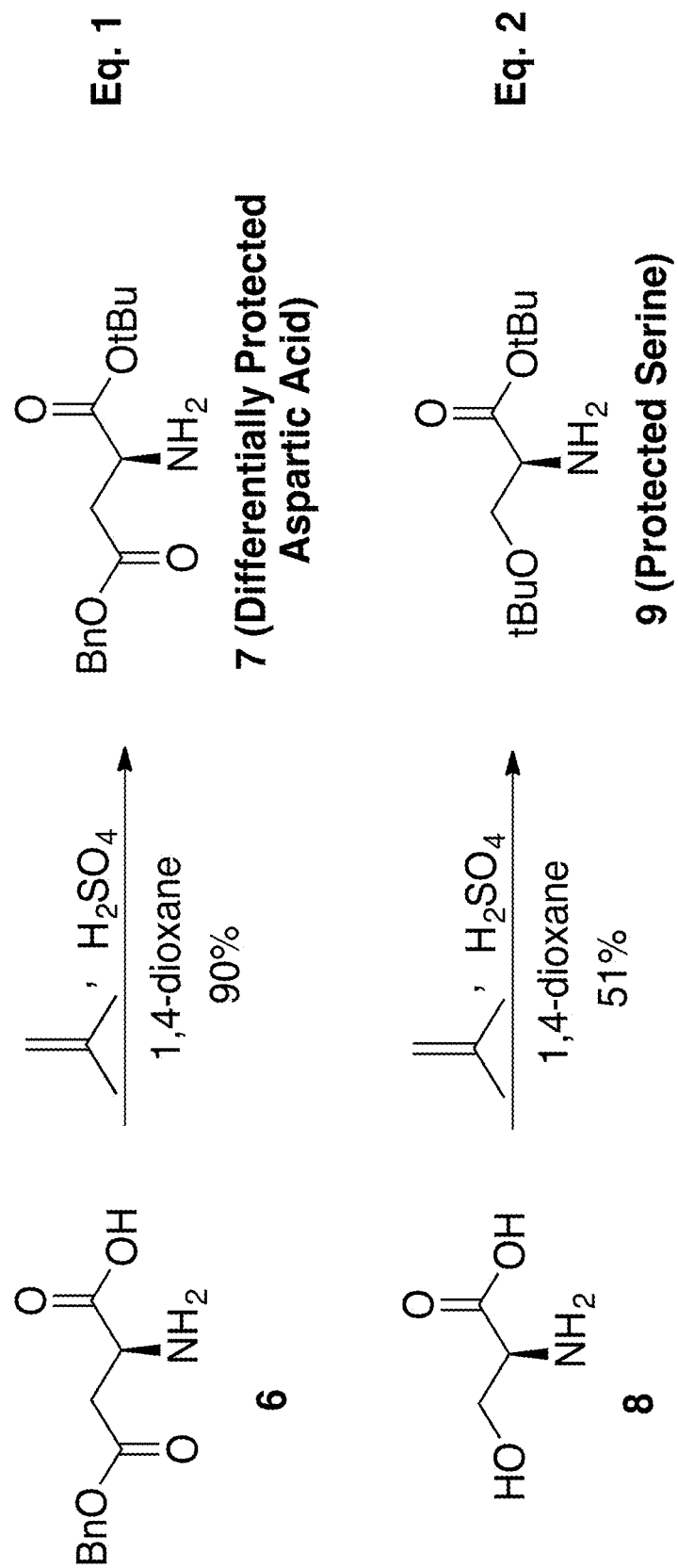
FIG. 13 is a graphic showing steps in production of avenic acid.

Next, the synthesis of tert-butyl L-☐-benzylaspartate (7) and L-(O-tert-butyl)-serine tert-butyl ester (9) were both conveniently prepared by treating their commercially available precursors with isobuytlene and $H_2SO_4$ in dioxane. See FIG. 13.

Figure 14:
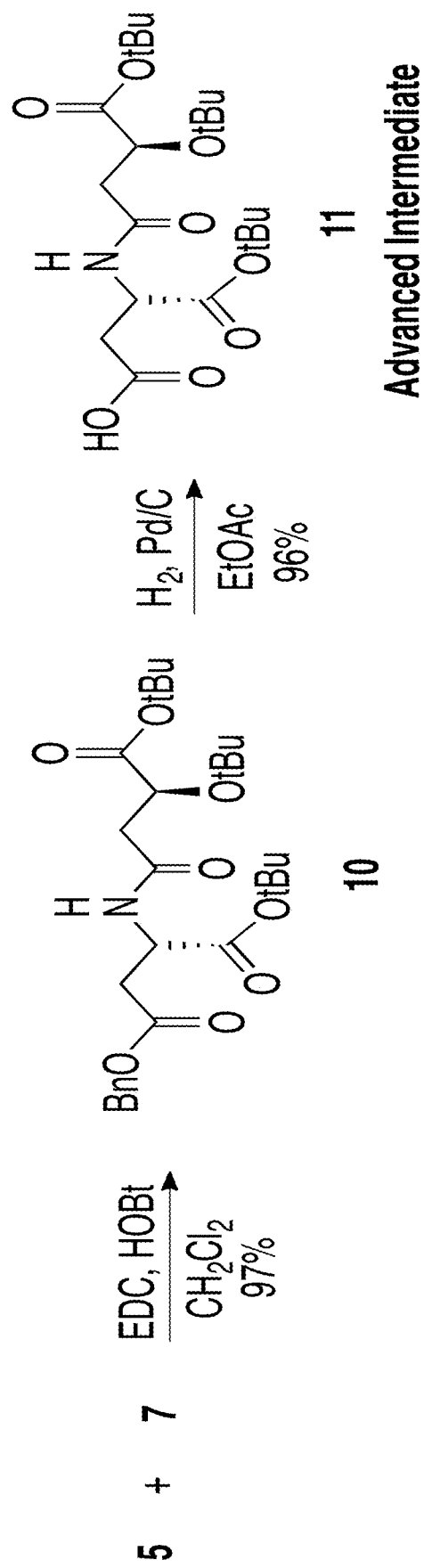
FIG. 14 is a graphic showing steps in production of avenic acid.

Then, EDC/HOBt coupling of 5 and 7 gave amide 10 which was then treated with hydrogen and Pd/C to afford our key, advanced intermediate 11 in excellent yield. See FIG. 14.

Figure 15:
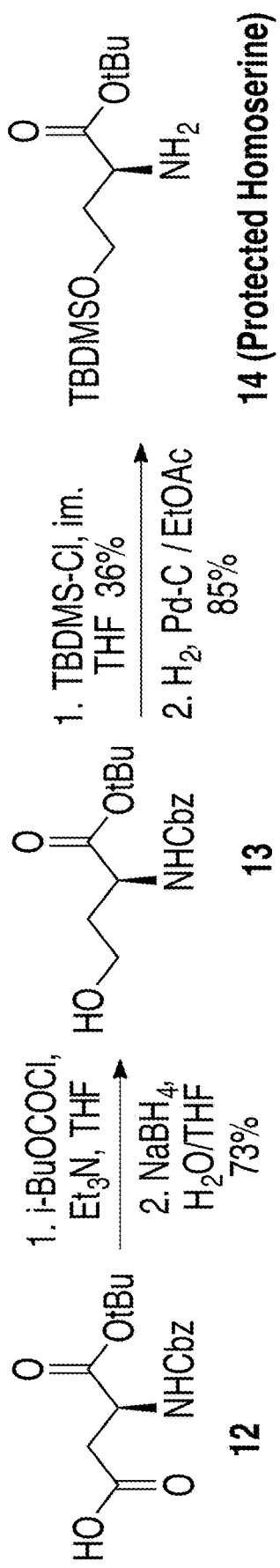
FIG. 15 is a graphic showing steps in production of avenic acid.

The synthesis of Avenic Acid 1 required the preparation of differentially protected homoserine 14. This was achieved via the reduction of the anhydride of commercially available tert-butyl L-(N-Cbz) aspartate (12) to give protected homoserine 13. Protection of the alcohol of 13 as the TBDMS ether followed by removal of the Cbz group afforded 14 which was ready for coupling to the advanced intermediate 11. See FIG. 15.

Figure 16:
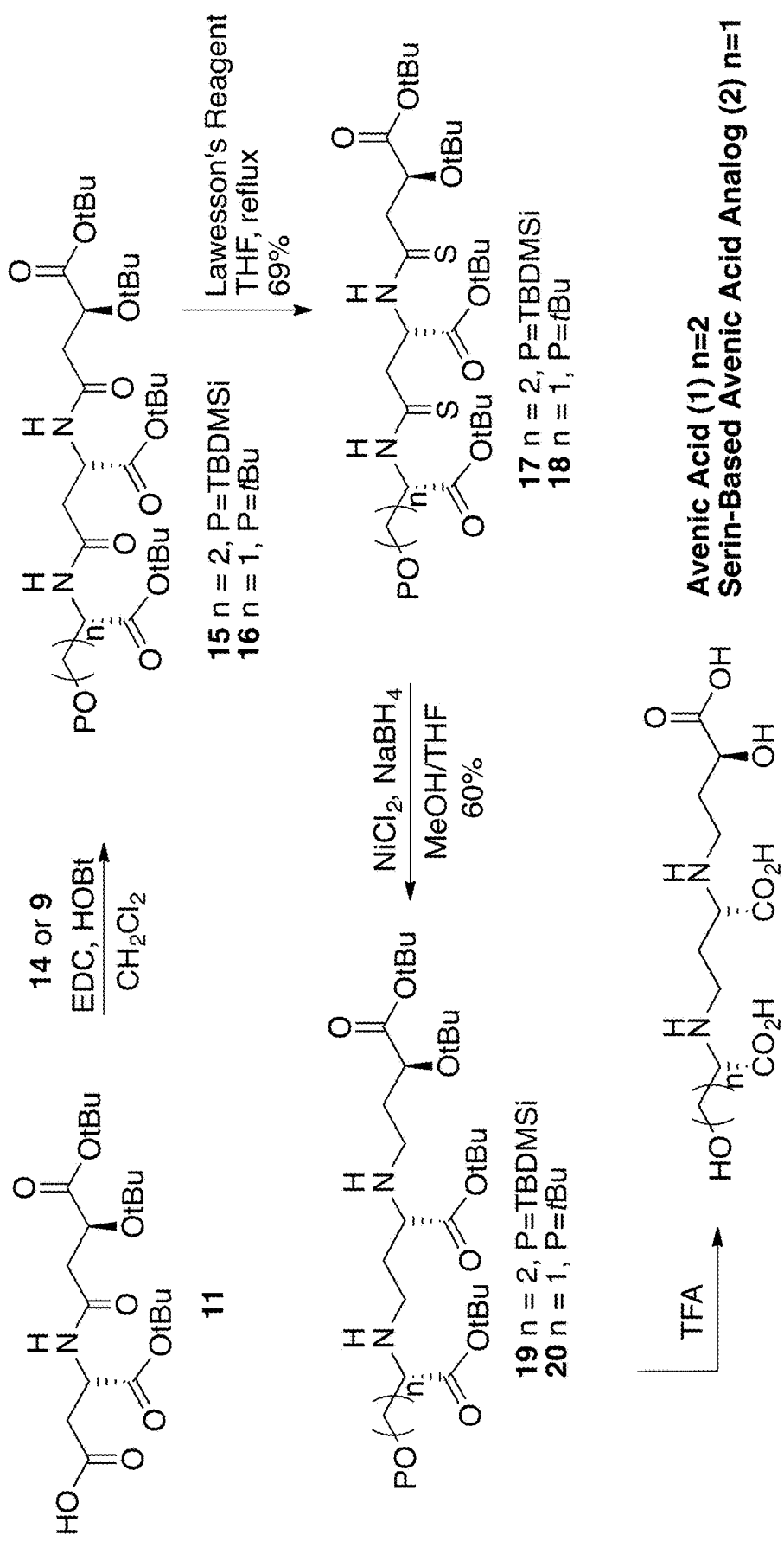
FIG. 16 is a graphic showing steps in production of avenic acid and serine analog.

Advanced intermediate 11 was then coupled to either 14 or 9 using EDC/HOBt conditions to yield di-amides 15 or 16 respectively. Both 15 and 16 were successfully converted to di-thioamides 17 and 18 with Lawesson's reagent. $NiCl_2$/ $NaBH_4$ reduction of both 17 and 18 gave fully protected avenic acid 19 and the serine-based analog 20. Finally, removal of the protecting groups with TFA followed by trituration with methanol and ether afforded both avenic acid 1 and serine-analog 2. See FIG. 16.

Figure 17:
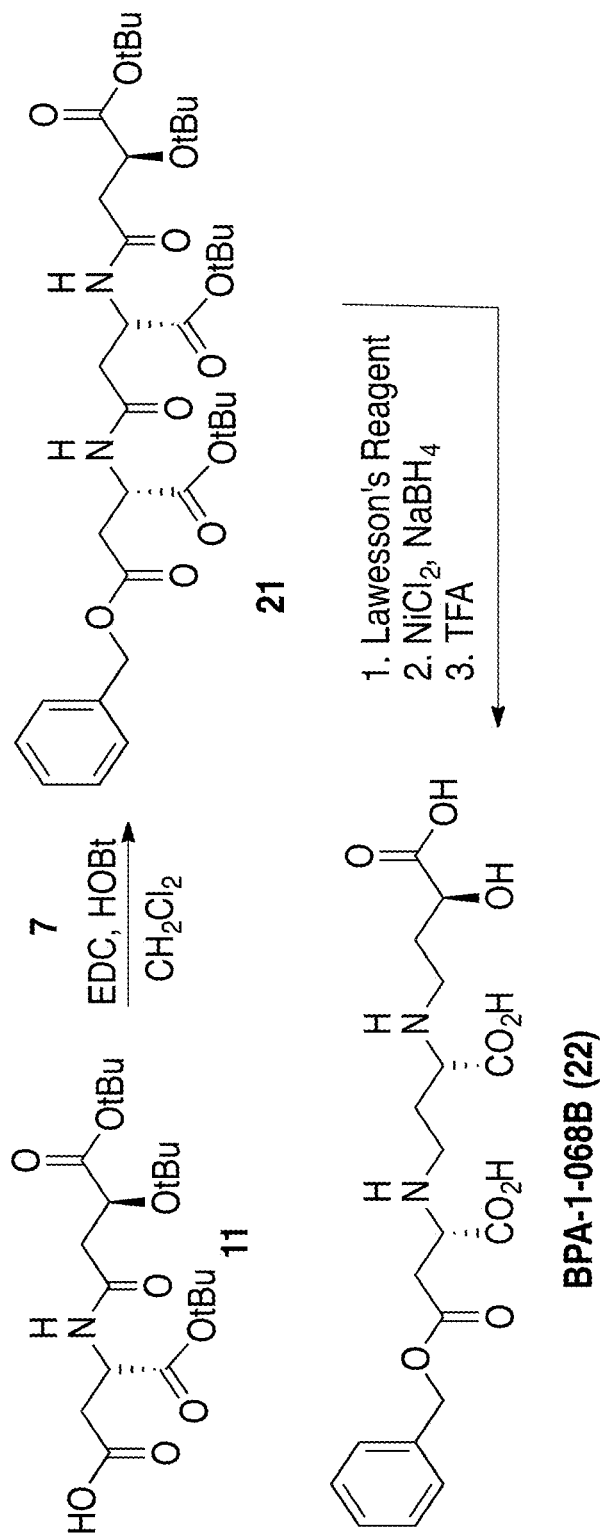
FIG. 17 is a graphic showing steps in production of BPA-1-068B.

BPA-1-068B
Synthesis of BPA-1-068B (22) was synthesized in analogous fashion. That is, advanced intermediate 11 was coupled to 7 to yield di-amide 21 which was then subsequently converted to the di-thioamide, reduced, and deprotected to give BPA-1-068B (22). See FIG. 17

Figure 18:
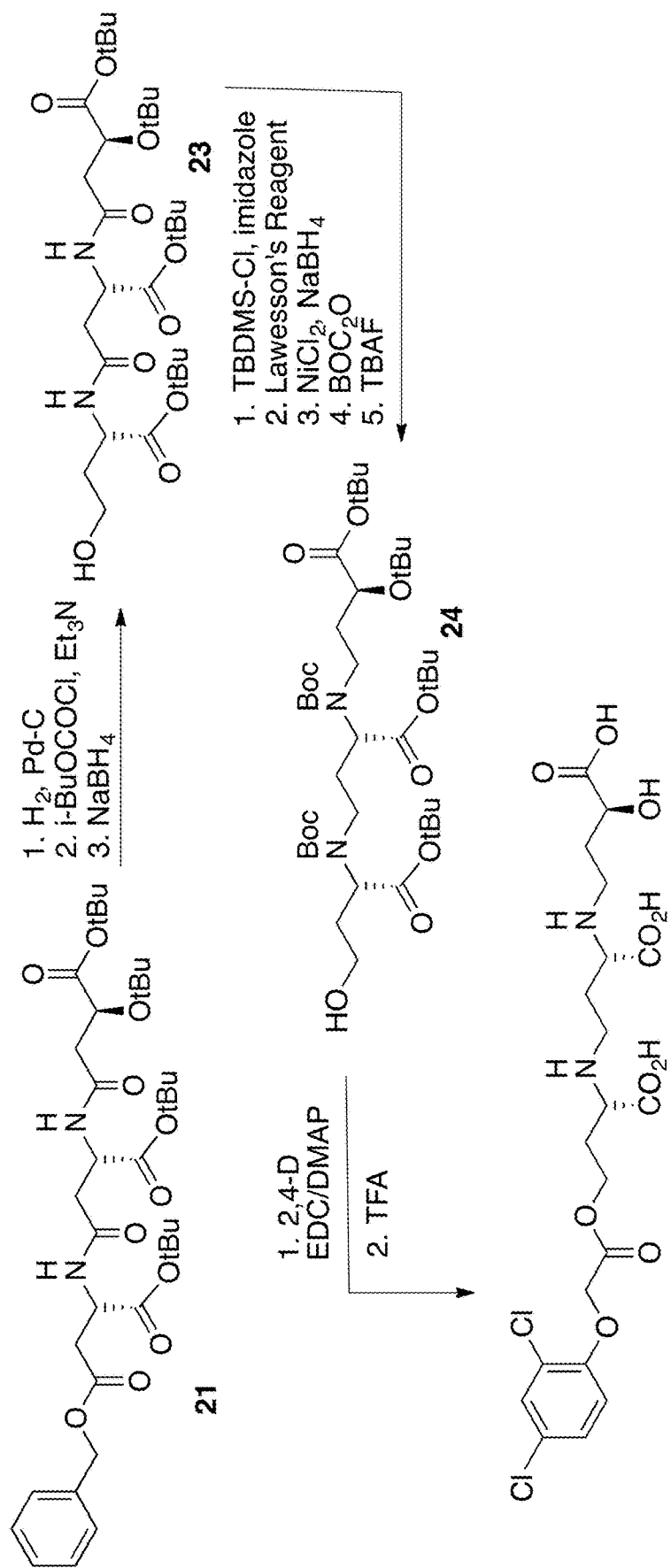
FIG. 18 is a graphic showing steps in production of MGS-2-198BF.

Conjugate of 2,4-D to Avenic Acid
The synthesis of 2,4-D conjugated to avenic acid (MGS-2-198BF) (25) began with removing the benzyl protecting group of 21 with hydrogen and Pd—C. The resulting carboxylic acid was converted to the alcohol 23 via the reduction of its anhydride. Alcohol 23 was then protected as a TBDMSi ether, and its amides converted to thioamides which were reduced as above. Next, the resulting amines were protected with the BOC group followed by removal of the TBDMSi group with TBAF to give alcohol 24. Finally, EDC/DMAP coupling of 24 with 2,4-D followed by TFA removal of the protecting groups afforded conjugate MGS-2-198BF (25). See FIG. 18.

Figure 19:
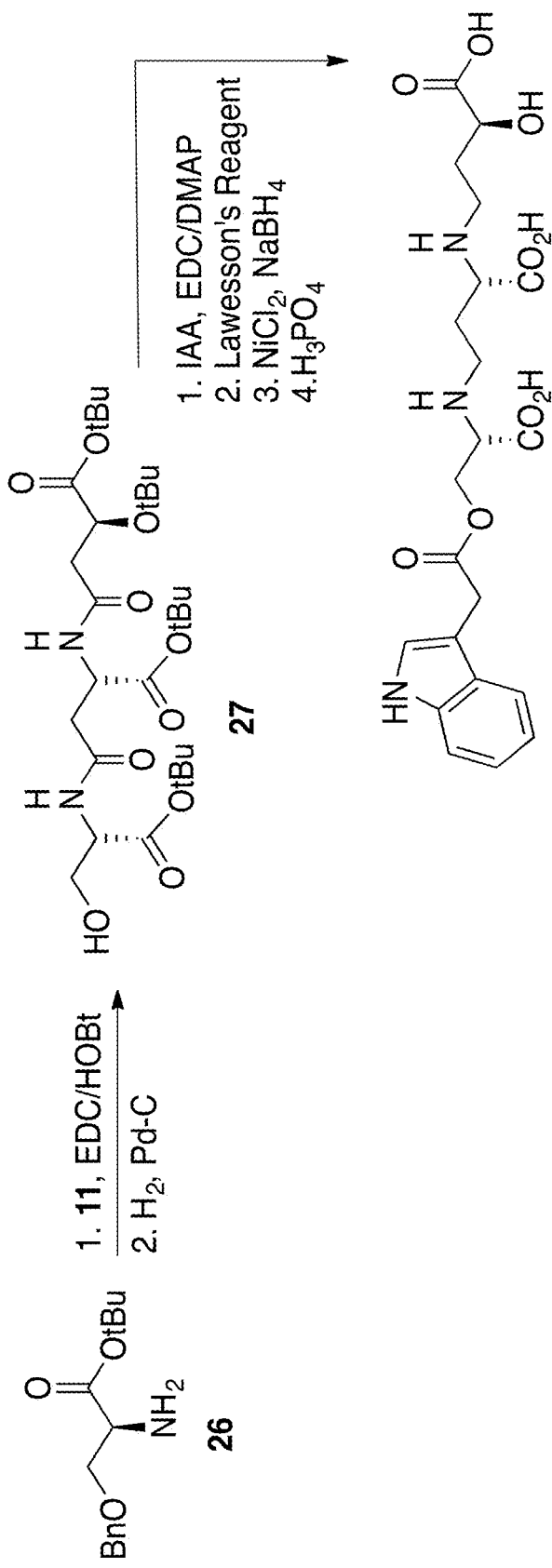
FIG. 19 is a graphic showing steps in production of MGS-1-186ppt.
Figure 23A:
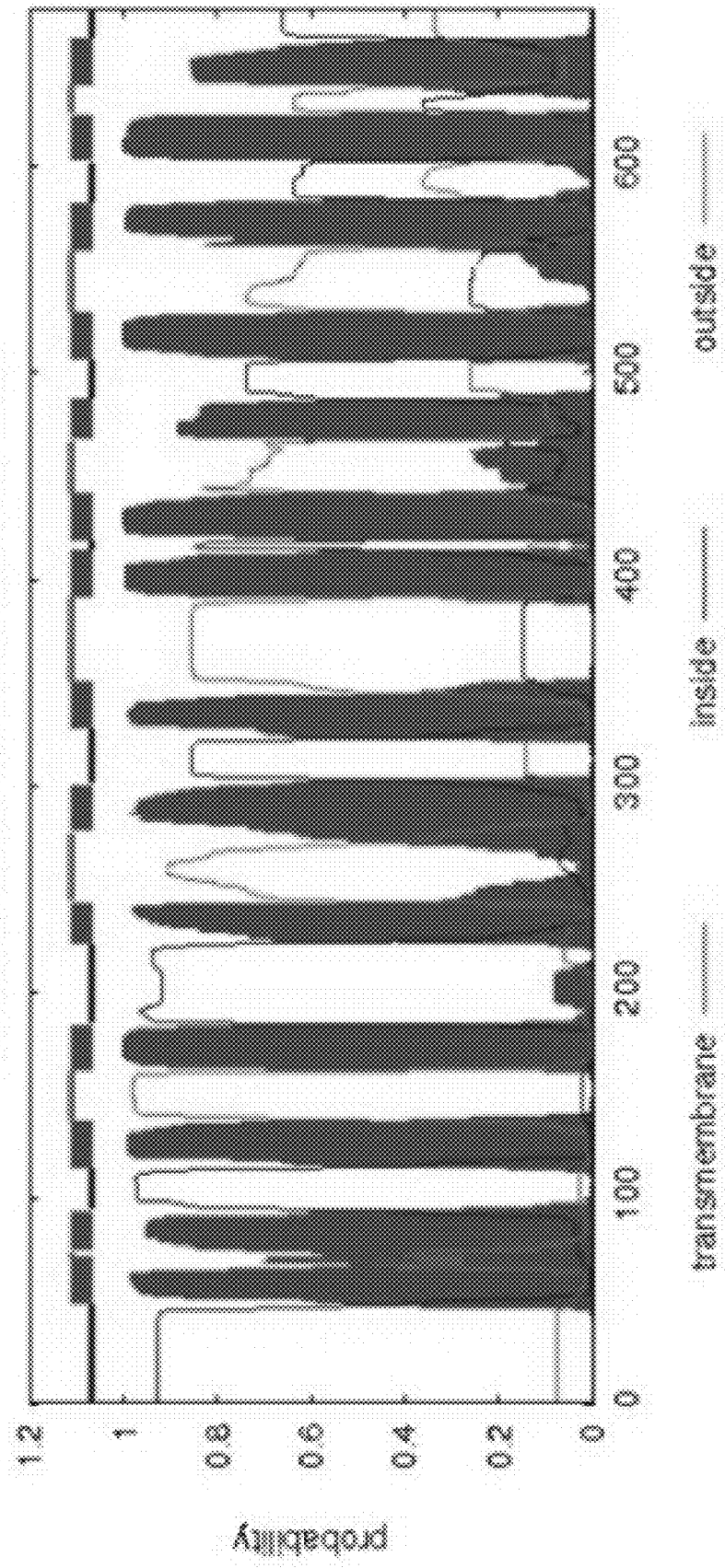
FIGS. 23A-C are graphs showing comparison of transmembrane protein predictions of three proteins, and color versions are necessary to distinguish different aspects of the protein in the graphs.
Figure 23B:
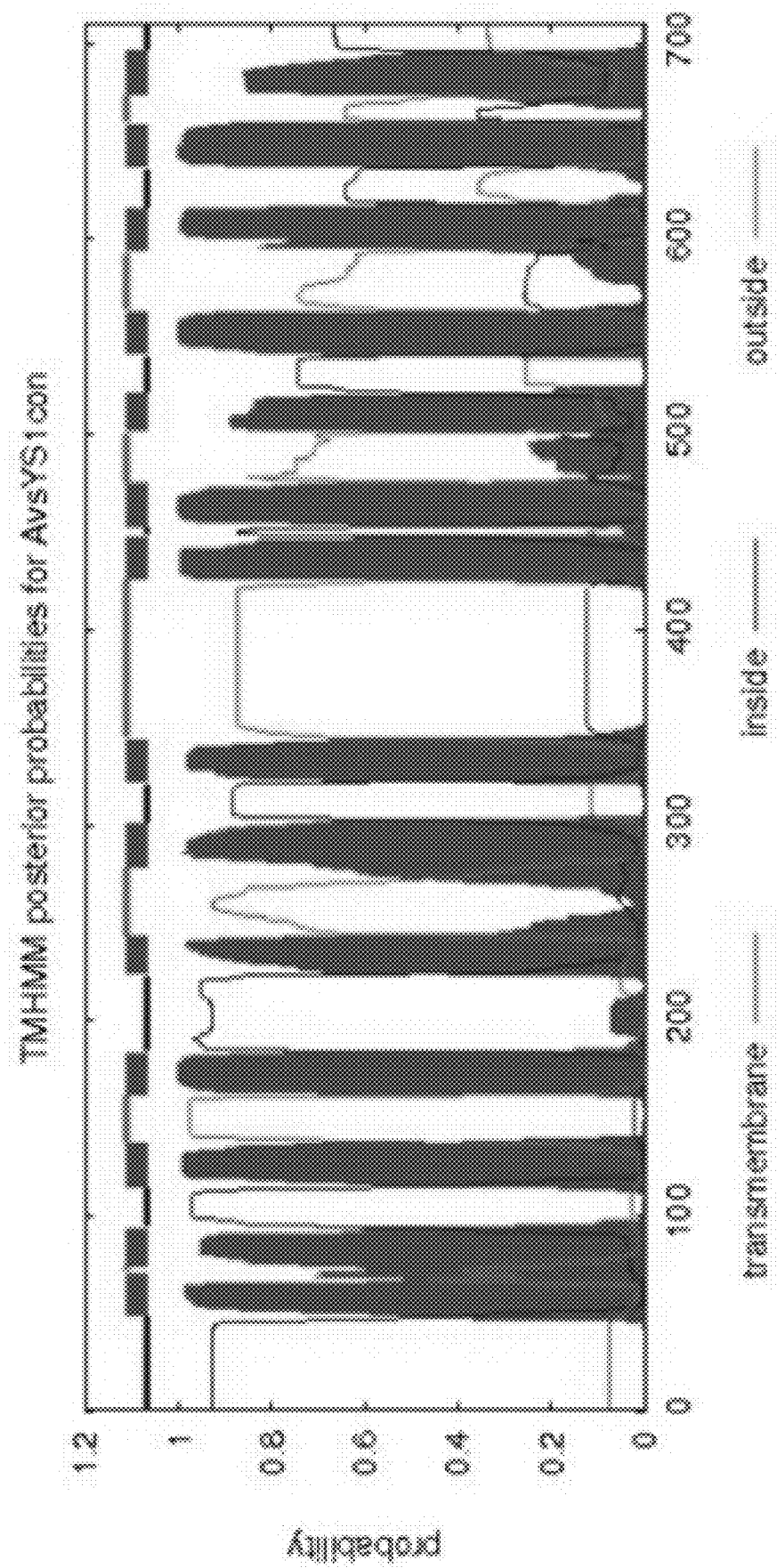
Figure 23C:
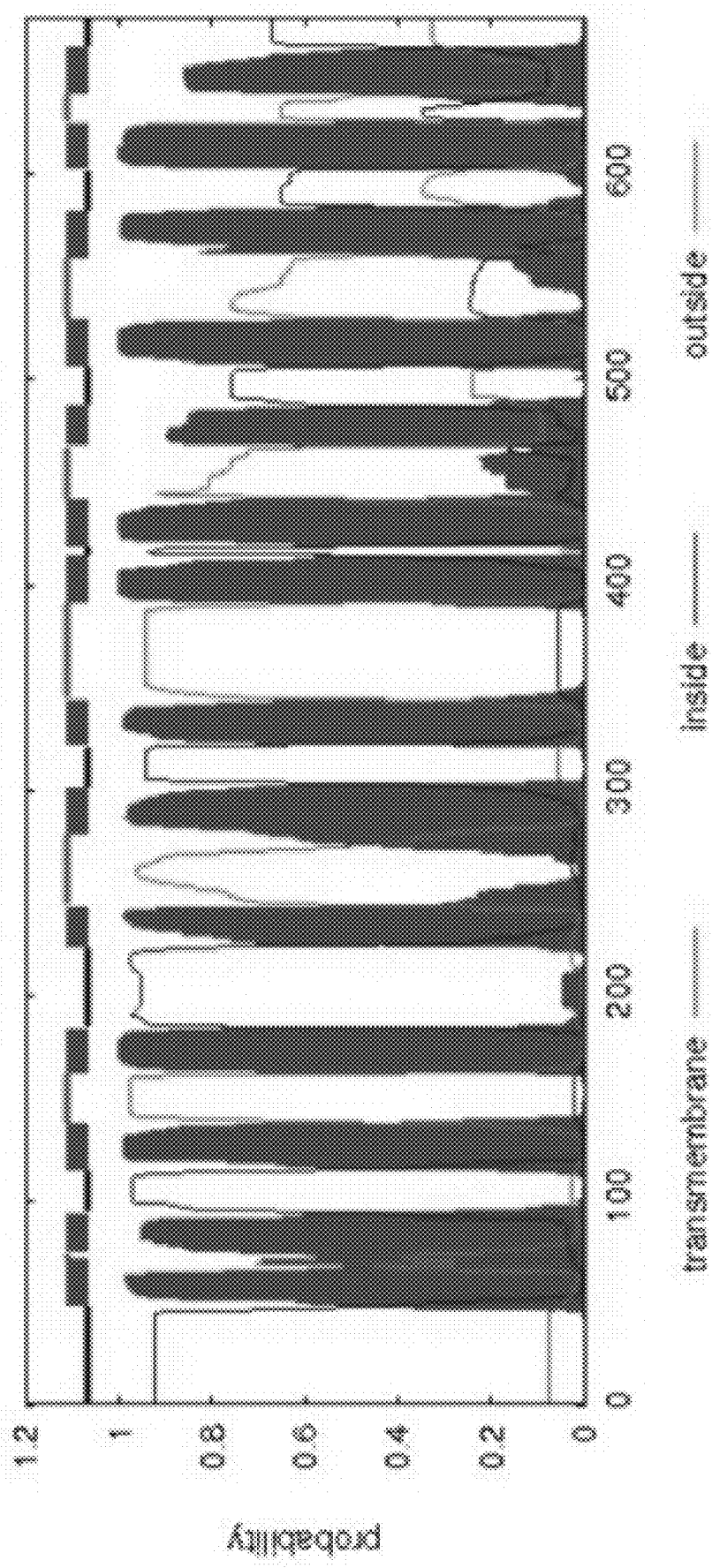
Figure 24:
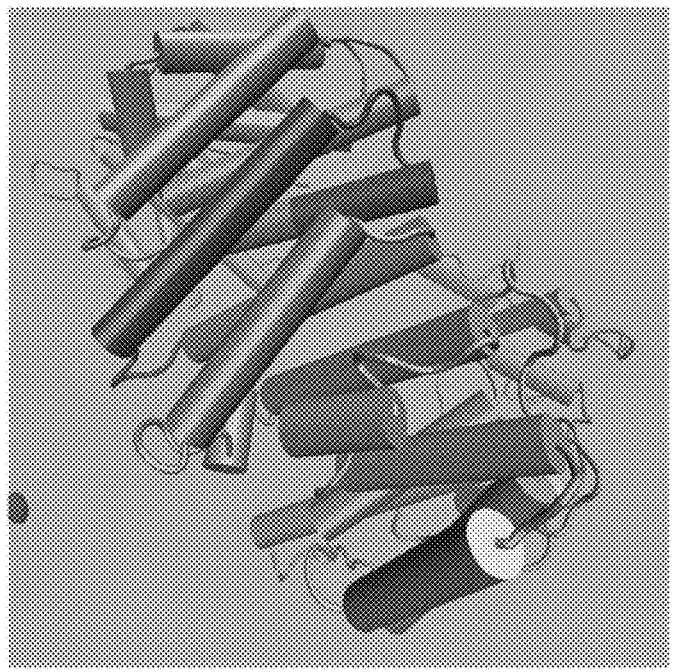
FIGS. 24, 25 and 26 are graphics showing model predictions of three proteins and it would not be possible to distinguish different sections of the protein without color.
Figure 25:
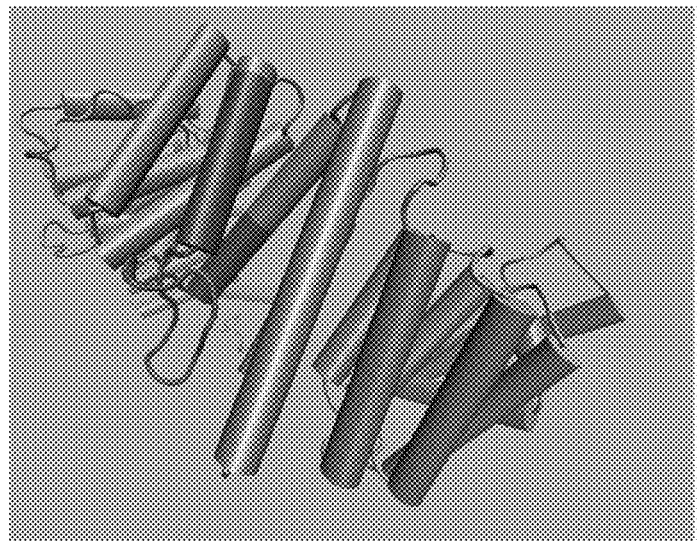
Figure 26:
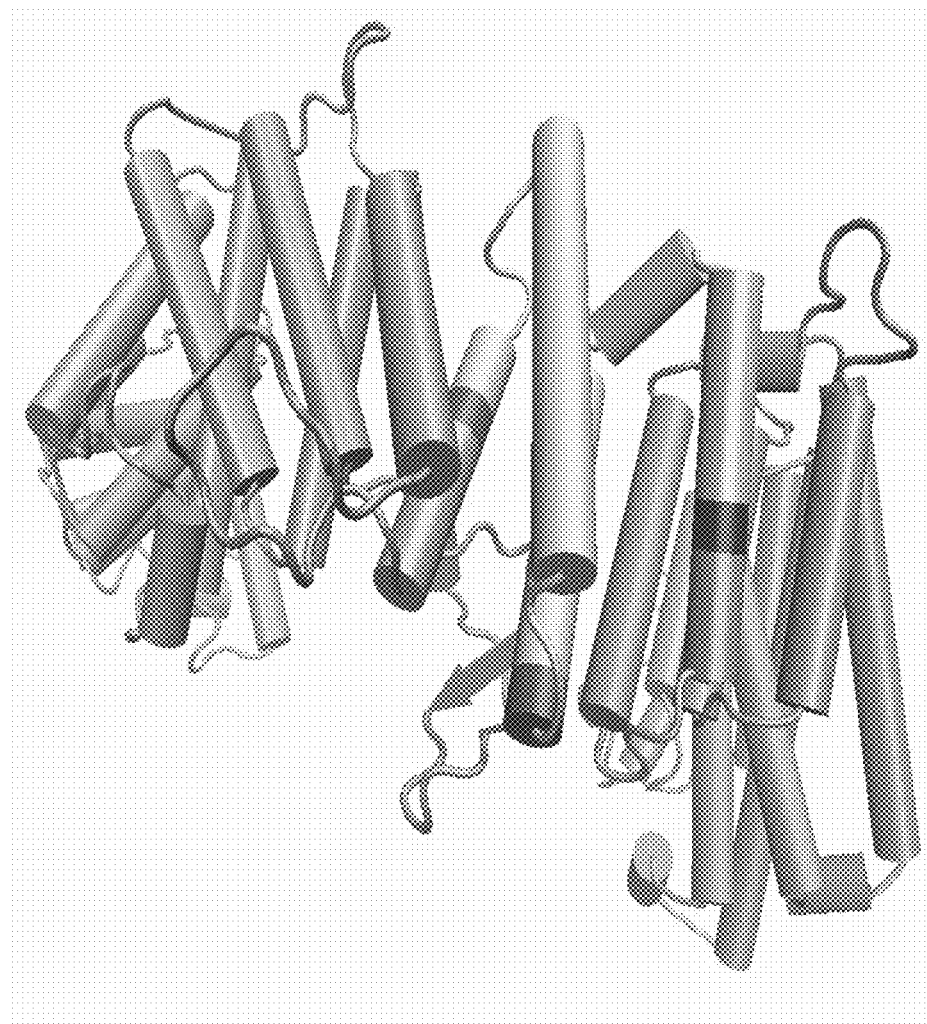

Conjugate of IAA to Serine Analog
The synthesis of Indole Acetic Acid (IAA) conjugated to serine analog of avenic acid (MGS-2-186ppt) (28) began with the EDC/HOBt coupling of advanced intermediate 11 with L-(O-benzyl)-serine tert-butyl ester 26. The resulting di-amide was treated with hydrogen and Pd—C to give alcohol 27. Next, EDC/DMAP coupling of 27 with IAA followed by treatment with Lawesson's Reagent, reduction of the resulting thioamides, and finally removal of the protecting groups with $H_3PO_4$ gave conjugate MGS-2-186ppt (28). See FIG. 19.

Conjugate of 2,4-D to Serine Analog
The following compound will be further evaluated.

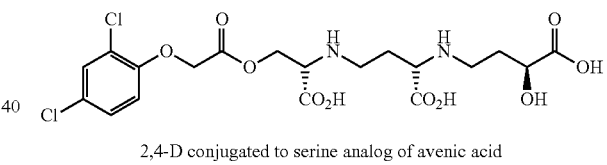

2,4-D conjugated to serine analog of avenic acid

Conjugate of IAA to Avenic Acid
The following compound will be further evaluated.

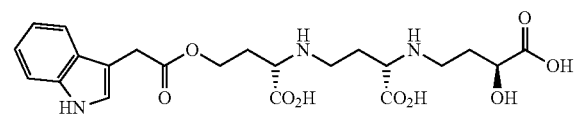

IAA conjugated to avenic acid

Conjugate of Salicylic Acid Conjugated to Serine Analog
The following compound will be further evaluated.

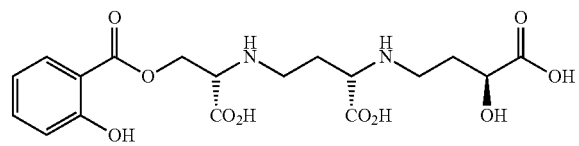

salicylic acid conjugated to serine analog of avenic acid

Conjugate of Salicylic Acid Conjugated to Avenic Acid
The following compound will be further evaluated.

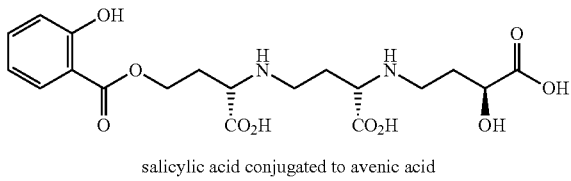

salicylic acid conjugated to avenic acid

Example 2

Confirmation of AvsYS1 as Avenic Acid/$Fe^{+3}$ Transporter

AvsYS1 (Genbank FJ477297.1) was isolated using 5'RACE from the roots of iron starved oats (*Avena sativa*). Primers were designed by comparing one functionally confirmed phytosiderophore/Fe' transporter (HvYS1) and other iron transport proteins. After obtaining a full-length clone, we subcloned the gene (AvsYS1) into a yeast galactose inducible expression vector (pYES2). The resultant plasmid was designated pJKD1. We obtained a yeast strain that lacks the ability to take up ferric iron, and transformed it with pYES2 and pJKD1. The transformants were grown under identical conditions in which the only iron available was in the $Fe^{+3}$/avenic acid complex. Our results showed that transformants containing pJKD1 were able to grow vigorously while those with pYES2 could not, providing functional confirmation that AvsYS1 is an avenic acid/$Fe^{+3}$ transporter.

As seen here, our most significant results were in the analysis of the AvsYS1 gene functionality in a yeast model system. We engineered the AvsYS1 gene into a galactose inducible expression systems vector (pYES2). Our first major result was the functional confirmation of the AvsYS1 gene. We transformed pYES2 and pJKD1 (pYES2/AvsYS1) into a strain of *S. cerevisiae* (DEY1453) that lacks the ability to take up $Fe^{+3}$. In the process, we developed a new assay based on growth in liquid medium. The advantage of this assay over more traditional assays used in yeast-based PS/$Fe^{+3}$ assays is that it is quantifiable. Other assays (e.g., Murata, 2006) grow yeast on a solid plate, and qualitative growth of colonies is used. With our assay, we can generate numerical data based on the density as measured by the absorbance at 600 nm. The DEY1453:pJKD1 exhibited robust growth under the experimental conditions whereas the DEY1453:pYES2 showed virtually no growth. Further detail is provided below.

Experiment A

53Y=DEY1453:pYES2 (no transporter)

53K=DEY1453:pJKD1 (pYES2/AvsYS1 [transporter])

DOB—Complete medium, supplemented w/$FeSo_4$, ampicillin 50

YNB-minimal medium, pH7.5, BPDS (ferrous chelator), ampicillin,

Experiment B

Avenic acid was synthesized linked to a benzyl group via an ester linkage as shown below. The growth in yeast in the presence of iron is impressive in that this larger attached group was able to be taken up the by avenic acid transporter.

A=Avenic Acid

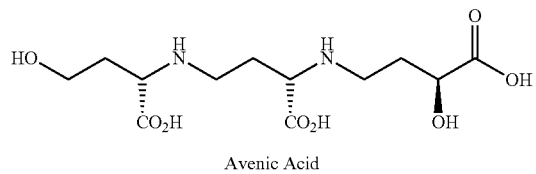

Avenic Acid

BPA-1-068B  (66 mg, 0.1 mmol)

BPA-1-068B

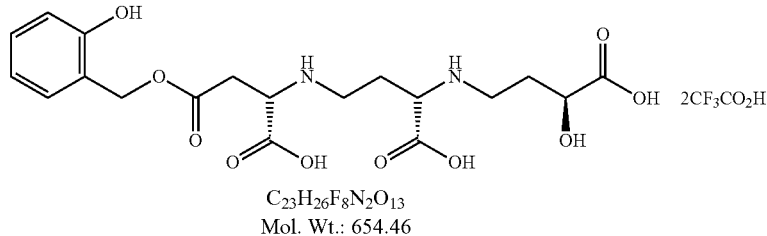

$C_{23}H_{26}F_8N_2O_{13}$
Mol. Wt.: 654.46

B=BPA-1068B

Ø=no supplementation

A.

Protocols included: 53Y and 53K in DOB+$FeSO_4$, 53Y and 53K in YNB supplemented with Avenic acid; 53Y and 53K supplemented with BPA-1-068B; 53Y and 53K in YNB w/no supplements; uninoculated YNB; uninoculated DOB.

53Y=DEY1453:pYES2 (no transporter)

53K=DEY1453:pJKD1 (pYES2/AvsYS1 [transporter])

DOB—Complete medium, supplemented w/$FeSo_4$, ampicillin 50

YNB-minimal medium, pH7.5, BPDS (ferrous chelator), ampicillin,

Ø=no supplementation

B.

Protocols included: 53Y and 53K, supplemented with Avenic acid, 53Y and 53K supplemented with BPA-1-068B, 53Y and 53K in YNB w/no supplements.

This experiment was repeated several times, and the 3K strain grown in YNB/avenic acid is now used as a positive control.

3Y=DEY1453:pYES2 (no transporter)

3K=DEY1453:pJKD1 (pYES2/AvsYS1 [transporter])

Strains grown in YNB/Gal, pH 7.5, Amp$_{50}$, Avenic acid: Fe$^{+3}$, 5:1

Evaluation of Uptake of Analog BPA-1-068B by the AVSYS1 Protein

Another interesting observation was made in relation to growth of the DEY1453:pJKD1 using one of the analogs complexed with Fe$^{+3}$. We were able to demonstrate that the pJKD1 containing strain was able to grow when ferric iron was supplied with analog BPA-1-068B (supra). This was a very significant result because it provided strong (though not dispositive) evidence in support of our Trojan Horse delivery technology. BPA-1-068B is much larger than the native avenic acid and has a very large hydrophobic group attached. As one would predict, the growth rate was slower, but undeniably robust when compared to DEY1453:pYES2 controls.

Protocols included: 53Y(pYES2) and 53K (pJKD1=pYES2+AvsYS1), supplemented with Avenic acid (red arrows); 53Y and 53K supplemented with BPA-1-068B (blue arrows); 53Y and 53K in YNB w/no supplements.

Example 3

Modified Avenic Acid Analogs

The generation of a vast array of effector molecules and organic analogues is limited by currently available organic synthesis methods. In one example of methods to speed up the synthesis process, an analog is produced that is one carbon shorter in the avenic acid primary carbon chain but would still chelate Fe$^{+3}$, that is MGS-2-128BF, described above. We compared this analog (MGS-2-128BF) and found that it supported growth as well as avenic acid. This finding is important for two reasons:

1. It showed that the AvsYS1 transporter can recognize carriers other than avenic acid, and
2. The smaller molecule will give us more freedom in evaluating analogs with larger effector groups.

This is very promising because this shortcut may reduce the time required for synthesis. Larger effector groups include, for example, those spatially larger than the phytosiderophore itself. One example provides for a molecular weight great than 250.

Example 4

Mutagensis of the Putative Specificity Region

We have synthesized a mutant transporter that has an external loop that is 34 amino acids larger than the standard loop at this region. Using multiple sequence alignment analysis, we have identified a region common to phytosiderophore transporters (confirmed and putative) that is extremely variable, and thus may be associated with specificity of uptake. Using PCR, we mutagenized the AvsYS1 gene so that it has 2 Sal1 restriction sites flanking the region of interest, 51 nucleotides encoding 17 amino acids. Ab initio modeling analysis and visualization suggests that these modifications altered the shape of the region, enlarging the external loop significantly. See FIG. 20 which shows the transporter nucleotide sequence of AvsYS1Sal, which is SEQ ID NO: 3 with the section in italics showing the region for modification (SEQ ID NO: 4) and the section in bold and underlined showing Sal 1 restriction cites. The Sal1 sites result in substitutions at residues 349, 350, 383 and 384. The translation of this sequence is shown in FIG. 21 (SEQ ID NO: 5) with the region identified for modification in italics (SEQ ID NO: 6). The AvsYS1Con entire nucleotide sequence is SEQ ID NO: 7. The resulting translation is SEQ ID NO: 8 shown in FIG. 22 with the 34 amino acid inserted region in italics (SEQ ID NO: 9).

Comparison of transmembrane predictions is shown in FIG. 23A (AvsYS1:351-391), B (AvsYS1Sal: 345-391) and C (AvsYS1Con: 3435-425). FIG. 24 shows Ab initio model predictions of AvsYS1 and FIG. 25 shows model predictions of AvsYS1Sal. The external loop of 345-391 is highlighted in red. There is increased size of the unstructured loop and reduced size of the external helix. FIG. 26 shows AvsYS1Con with red and yellow sections showing the 345-425 region.

We have confirmed that the mutated gene can be forced to recognize and take up avenic acid/Fe+3, and have obtained mutant yeast strains to evaluate specificity of uptake for Mn, Cu, and Zn. One goal of creating the Sal1 mutant (designated AvsYS1Sal) will serve as a template to generate a library of randomly mutagenized inserts that will be ligated into the parent plasmid. A plasmid has been created that has the modified transporter that will be subject to random mutagenesis.

We will further generate a library of mutant PS/$Fe^{+3}$ transporters, thus expanding the repertoire of PS analogs recognized by the transporter. By mutagenizing this external loop of the AvYS1 protein, the transporter's specificity should be modified and may allow us to identify useful mutants by screening on media containing the avenic acid analog in question, complexed with ferric iron. We have constructed a second transporter that will be used to generate a mutant library using random mutagenesis PCR. Mutants will be evaluated for their ability to recognize native avenic acid as well as with analogs.

The generation of a mutant library will be done as follows.

a. Using pAvsYS1Sal as a template, we will amplify the 51 bp region of interest under low stringency conditions (substitute $Mn^{+2}$ for $Mg^{+2}$, use an imbalance of nucleotides, and dope the reaction with dITP).

b. After the first round of PCR, the product will be isolated, gel purified, and used as a template for a second reaction under similar conditions to the first.

c. Products will ligate into plasmids and transformed into *E. coli.* d. Colonies will be grown in liquid culture and plasmids will be purified and sequenced to determine the efficiency of our procedure.

e. Adjustments will be made based on the data from 4d, and clones with the most mutations will be used for the next round of mutagenesis.

f. When sufficient numbers of mutants are obtained, they will be pooled and we will do a large scale plasmid isolation.

g. Plasmids will be digested with Sal1 and ligated into the yeast vector pYES2.

h. Yeast will be transformed and plated under appropriate Fe-limiting conditions. For example, they would be grown on plates in which the only source of iron was iron complexed with an avenic acid-2,4-D conjugate.

See 1b, 1c. Any compounds found to support yeast growth under the conditions described above will be cloned into an *Agrobacterium* vector and used to transform tomatoes or other plant of our choice.

Example 5

Experiments with Transgenic Tomatoes

We received eleven transgenic tomatoes (cv. MicroTom, MT*) and confirmed the presence of the AvsYS1 gene using PCR. Plants were grown through the summer and hundreds of seeds collected.

In one experiment, transformants (MT*) and non-transformed MicroTom (MT) were grown under alkaline conditions (pH>7.5) in *solium* companion planted with oats, the natural source of avenic acid. Seedlings were started in a soil free potting mix transplanted into ProMix in which the pH was raised and maintained with hydrated lime and 12.5 mM HEPES to ~7.5. Four MT* and four MT of identical size and development were intercropped with oats, the natural source of avenic acid. Plants were regularly fed with ½ strength modified Hoagland's solution (—Fe)/12.5 mM HEPES 7.5, 5 µM BPDS, and 10 µM $Fe^{+3}$. These conditions and additives are designed to maintain iron in the ferric state and sequester iron in the ferrous state using BPDS as a ferrous iron chelator. Again, the small sample size precludes any dispositive interpretations, but some of the MT* visibly outgrew all MT under these conditions and showed more resistance to *Septoria*, a fungal infection that plagues our greenhouse (FIGS. 4 and 5). This companion planting is a novel strategy that is expected to improve $Fe^{+3}$ uptake in transformants expressing the AvsYS1 gene, and we will repeat this experiment on a larger scale.

We will also be able to increase the size of our sample in an experiment in which we will grow plants hydroponically. This will give us more control over maintaining pH, nutrients, pathogens, etc. Seeds of MT* and MT have been aseptically planted on ½ strength Murashige-Skoog with organics (MSO). When the second set of true leaves emerge, expression analysis will be conducted using RT/PCR on total RNA. Those that have the highest AvsYS1 expression levels will be transferred to hydronic growth conditions and maintained with Hoagland's solution (—Fe). pH will be maintained at pH 7.5-8.0 for experimental plants (MT* and MT) and iron will only be provided as the avenic acid/$Fe^{+3}$ complex. Controls (MT* and MT) will be grown under standard conditions and maintained with complete Hoagland's solution containing Fe-EDTA. In addition to expression analysis, other measures will include western blotting and chlorophyll fluorescence in leaves, as well as evaluating vigor as manifested in total weight, shoot length, and weights of roots and shoots. Plants will be grown to fruiting stage, and we will measure iron content on a total and per gram basis of leaves and fruits. Once growth conditions are optimized we will evaluate the effects of Trojan Horse analogs as they become available.

We are attaching a natural plant growth hormone (indole acetic acid) and a synthetic growth hormone (2,4-D) with which we will be able to dramatically assess our "Trojan Horse" targeted delivery system based on an exaggerated growth response induced by the uptake of either of these molecules.

---

What is claimed is:

1. A method of delivering a molecule to a plant, the method comprising,
   a) modifying a plant by:
      i) introducing a modified avenic acid transporter into a plant; or
      ii) modifying an avenic acid transporter in an *Avena sativa* plant;
      iii) said modified avenic acid transporter;
   b) said modified plant uptaking avenic acid or a functional analog thereof, and a molecule conjugated with said avenic acid or functional analog thereof, and
   c) delivering said avenic acid, functional analog thereof or conjugated molecule to said modified plant.

2. The method of claim 1, wherein said plant is a non-graminaceous plant.

3. The method of claim 1, wherein said plant is a dicotyledonous plant.

* * * * *

UNITED STATES PATENT AND TRADEMARK OFFICE
CERTIFICATE OF CORRECTION

| | |
|---|---|
| PATENT NO. | : 10,563,216 B2 |
| APPLICATION NO. | : 15/488954 |
| DATED | : February 18, 2020 |
| INVENTOR(S) | : George T. Davis and Mark Stocksdale |

Page 1 of 1

It is certified that error appears in the above-identified patent and that said Letters Patent is hereby corrected as shown below:

In Column 59, Claim 1, Line 27:
INSERT --having at least 98% identity to SEQ ID NO: 8-- between "transporter" and ";".

Signed and Sealed this
Nineteenth Day of May, 2020

Andrei Iancu
*Director of the United States Patent and Trademark Office*

SEQUENCE LISTING

```
<160> NUMBER OF SEQ ID NOS: 9

<210> SEQ ID NO 1
<211> LENGTH: 676
<212> TYPE: PRT
<213> ORGANISM: Avena sativa

<400> SEQUENCE: 1

Met Asp Val Leu Gly Pro Asp Arg Thr Arg Ile Ala Pro Glu Ile Glu
1               5                   10                  15

Lys His Val Ala Ala Glu Gly Asp Arg Glu Ser Asp Pro Ala Leu Ala
            20                  25                  30

Ala Glu Arg Glu Leu Glu Pro Leu Gly Arg Trp Gln Asp Glu Leu Thr
        35                  40                  45

Val Arg Gly Met Val Ala Ala Leu Leu Ile Gly Phe Ile Tyr Thr Val
    50                  55                  60

Ile Val Met Lys Ile Ala Leu Thr Thr Gly Leu Val Pro Thr Leu Asn
65                  70                  75                  80

Val Ser Ala Ala Leu Leu Ser Phe Leu Ala Leu Arg Gly Trp Thr Arg
                85                  90                  95

Leu Leu Asp Arg Phe Gly Ile Val Ser Arg Pro Phe Thr Arg Gln Glu
            100                 105                 110

Asn Thr Ile Val Gln Thr Cys Gly Val Ala Cys Tyr Thr Ile Ala Phe
        115                 120                 125

Ala Gly Gly Phe Gly Ser Thr Leu Leu Gly Leu Asn Lys Asn Thr Tyr
    130                 135                 140

Glu Leu Ala Gly Asp Ser Pro Gly Asn Gly Pro Gly Ser Tyr Lys Glu
145                 150                 155                 160

Pro Gly Ile Gly Trp Met Thr Ala Phe Leu Phe Ser Cys Ser Phe Gly
                165                 170                 175
```

```
Gly Leu Leu Thr Leu Ile Pro Leu Arg Gln Val Leu Val Asp Tyr
            180                 185                 190

Arg Leu Val Tyr Pro Ser Gly Thr Ala Thr Val Leu Ile Asn Gly
            195                 200                 205

Phe His Thr Ala Gln Gly Asp Lys Asn Ser Arg Lys Gln Ile Arg Gly
    210                 215                 220

Phe Leu Lys Tyr Phe Gly Gly Ser Phe Leu Trp Ser Phe Gln Trp
225                 230                 235                 240

Phe Tyr Thr Gly Gly Asp Val Cys Gly Phe Ile Gln Phe Pro Thr Phe
            245                 250                 255

Gly Leu Lys Ala Trp Lys Gln Thr Phe Phe Asp Phe Ser Leu Thr
            260                 265                 270

Tyr Ile Gly Ala Gly Met Ile Cys Pro His Ile Val Asn Ile Ser Thr
            275                 280                 285

Leu Leu Gly Ala Ile Leu Ser Tyr Gly Ile Leu Trp Pro Leu Ile Ser
            290                 295                 300

Lys Asn Lys Gly Asp Trp Tyr Pro Ala Asp Val Lys Glu Ser Ser Met
305                 310                 315                 320

Lys Ser Leu Tyr Gly Tyr Lys Ala Phe Ile Cys Ile Ala Leu Ile Met
                325                 330                 335

Gly Asp Gly Leu Tyr His Phe Thr Lys Ile Ile Thr Ile Thr Cys Lys
            340                 345                 350

Gly Met Tyr Arg Gln Phe Ser Arg Lys His Ala Asp Asn Arg Glu Lys
            355                 360                 365

Asn Val Asp Asn Thr Val Ser Leu Glu Asp Leu Gln Arg Asp Glu Val
    370                 375                 380

Phe Lys Arg Gly His Leu Pro Ala Trp Ile Ala Tyr Ser Gly Tyr Ala
385                 390                 395                 400

Val Leu Ser Val Val Ala Val Thr Thr Pro Ile Met Phe Arg Gln
            405                 410                 415

Val Lys Trp Tyr Tyr Val Val Ile Ala Tyr Val Val Ala Pro Met Leu
            420                 425                 430

Gly Phe Ala Asn Ser Tyr Gly Thr Gly Leu Thr Asp Ile Asn Met Gly
            435                 440                 445

Tyr Asn Tyr Gly Lys Ile Gly Leu Phe Val Phe Ala Gly Trp Ala Gly
            450                 455                 460

Arg Asp Asn Gly Val Val Ala Gly Leu Val Val Gly Thr Cys Val Lys
465                 470                 475                 480

Gln Leu Val Leu Ile Ser Ala Asp Leu Met Gln Asp Phe Lys Thr Ser
                485                 490                 495

Tyr Leu Thr Lys Thr Ser Pro Arg Ser Met Met Val Ala Gln Ala Ile
            500                 505                 510

Gly Thr Ala Met Gly Cys Val Val Ser Pro Leu Thr Phe Met Leu Phe
            515                 520                 525

Tyr Arg Ala Phe Asp Ile Gly Asn Pro Asp Gly Thr Trp Lys Ala Pro
            530                 535                 540

Tyr Ala Leu Ile Tyr Arg Asn Met Ala Ile Leu Gly Val Glu Gly Phe
545                 550                 555                 560

Ser Val Leu Pro Lys Tyr Cys Leu Ala Leu Ser Gly Gly Phe Phe Ala
            565                 570                 575

Phe Ala Ala Ile Leu Ser Ile Ala Arg Asp Phe Thr Pro His Arg Tyr
            580                 585                 590
```

```
       Arg Gln Tyr Val Pro Leu Pro Met Ala Met Ala Val Pro Phe Leu Val
                    595                 600                 605

Gly Gly Ser Phe Ala Ile Asp Met Cys Val Gly Ser Leu Val Val Phe
           610                 615                 620

Ile Trp Asn Lys Ile Asn Lys Lys Glu Ala Gly Phe Met Val Pro Ala
       625                 630                 635                 640

Val Ala Ser Gly Leu Ile Cys Gly Asp Gly Ile Trp Thr Phe Pro Ser
                       645                 650                 655

Ser Ile Leu Ala Leu Ala Lys Ile Thr Pro Pro Ile Cys Met Lys Phe
                   660                 665                 670

Thr Pro Ala Pro
                   675

<210> SEQ ID NO 2
<211> LENGTH: 2031
<212> TYPE: DNA
<213> ORGANISM: Avena sativa

<400> SEQUENCE: 2
```

| | | | | | |
|---|---|---|---|---|---|
| atggacgtcc | tgggccctga | ccgcacgcgg | atcgcgccgg | agatcgagaa | gcacgtggcc | 60 |
| gcggagggcg | acaggagtc | tgacccggcg | ctggccgcgg | agcggagct | agagcccctg | 120 |
| ggcggtggc | aggacgagct | gaccgtgcgg | ggcatggtgg | cggcgctgct | catcgggttc | 180 |
| atctacaccg | tcatcgtcat | gaagatcgcg | ctcaccaccg | ggctggtgcc | cacccctcaac | 240 |
| gtctccgccg | cgctgctctc | cttcctcgcg | ctccgcggct | ggacgcgctt | gctggaccgc | 300 |
| ttcggcatcg | tgtcccgtcc | cttcacgcgg | caggagaaca | ccatcgtcca | gacctgcggc | 360 |
| gtcgcctgct | acaccatcgc | gttcgccggt | ggcttcgggt | caaccttgct | gggtctaaac | 420 |
| aagaacacgt | acgagctggc | cggcgactcg | ccgggcaacg | gccgggggag | ctacaaggag | 480 |
| ccagggattg | gctggatgac | ggcattcctc | ttttcttgca | gcttcggggg | gctcctcacc | 540 |
| ttgattcccc | ttagacaggt | attggtcgtg | actatagat | tagtgtaccc | aagtgggacg | 600 |
| gcaactgctg | ttcttataaa | cggatttcat | accgctcaag | gagacaagaa | ctccaggaag | 660 |
| caaatccgtg | ggttcttgaa | gtacttcggg | ggtagctttt | tatggagctt | cttccagtgg | 720 |
| ttctacaccg | gcggcgacgt | tgtgggttc | attcagttcc | ctactttttgg | tctgaaggcc | 780 |
| tggaagcaga | cgttcttctt | tgactttagc | ctgacataca | tcggtgccgg | gatgatctgc | 840 |
| ccacatatag | taaatatctc | caccctcttg | ggtgcaattc | tttcttatgg | gatattgtgg | 900 |
| ccactcatca | gtaagaacaa | gggtgactgg | taccctgcag | atgtcaaaga | agcagcatg | 960 |
| aaaagtttgt | acggttacaa | ggccttcata | tgcatcgctc | tgatcatggg | ggatggactc | 1020 |
| taccacttca | ccaaaattat | taccatcact | tgcaagggca | tgtatcgaca | gttcagccgt | 1080 |
| aaacatgctg | acaaccgaga | gaaaaatgtg | gacaatacag | tctcactcga | ggatttgcag | 1140 |
| cgcgacgagg | tcttcaagag | gggccatctc | cccgcttgga | tcgcgtacag | tgggtatgcc | 1200 |
| gtgctgagcg | tcgttgcagt | ggttaccacg | ccaataatgt | tccgacaagt | gaaatggtac | 1260 |
| tacgtagtta | tagcctatgt | cgtcgccccc | atgcttggat | cgccaattc | ctacgggacg | 1320 |
| gggctcaccg | acatcaacat | gggctataac | tatggcaaga | tagggctctt | cgtcttcgcg | 1380 |
| ggttgggctg | gcagggacaa | tggtgtcgtt | gcaggtctgg | ttgttggtac | atgtgtgaag | 1440 |
| cagctggtgc | tgatatctgc | agatttgatg | caagacttca | agacgagtta | tctcactaag | 1500 |
| acatcaccaa | gatccatgat | ggtggcacag | gcaattggga | cagccatggg | ctgcgttgtc | 1560 |
| tctccccctta | cgttcatgct | cttctacagg | gcatttgata | ttggcaatcc | agatggtacc | 1620 |

```
tggaaggcac cgtatgcact gatataccgt aatatggcaa tactcggtgt ggagggcttc      1680
tcagtactgc ccaagtattg cctggcactc tctggtggat ttttcgcgtt tgcagcaatc      1740
ctcagcatag caagagattt cacgccgcat aggtataggc agtatgtgcc cctgccaatg      1800
gcgatggcgg ttccattcct tgtcggcggg agctttgcga ttgatatgtg tgtcgggagt      1860
ttggtggttt ttatctggaa caagataaac aagaaggagg ccggcttcat ggtccctgca      1920
gttgcatccg gtttgatatg tggggatggg atatggacat tcccttcgtc catacttgct      1980
cttgccaaga ttacaccacc aatttgcatg aagtttacac ctgcacccta g               2031

<210> SEQ ID NO 3
<211> LENGTH: 2031
<212> TYPE: DNA
<213> ORGANISM: Avena sativa

<400> SEQUENCE: 3
atggacgtcc tgggccctga ccgcacgcgg atcgcgccgg agatcgagaa gcacgtggcc        60
gcggagggcg acagggagtc tgacccggcg ctggccgcgg agcgggagct agagcccctg       120
gggcggtggc aggacgagct gaccgtgcgg ggcatggtgg cggcgctgct catcgggttc       180
atctacaccg tcatcgtcat gaagatcgcg ctcaccaccg gctggtgcc cacccctcaac       240 gtctccgccg cgctgctctc cttcctcgcg ctccgcggct ggacgcgctt gctggaccgc       300
ttcggcatcg tgtcccgtcc cttcacgcgg caggagaaca ccatcgtcca gacctgcggc       360
gtcgcctgct acaccatcgc gttcgccggt ggcttcgggt caaccttgct gggtctaaac       420
aagaacacgt acgagctggc cggcgactcg ccgggcaacg ggccggggag ctacaaggag       480
ccagggattg gctggatgac ggcattcctc ttttcttgca gcttcggggg gctcctcacc       540
ttgattcccc ttagacaggt attggtcgtg gactatagat tagtgtaccc aagtgggacg       600
gcaactgctg ttcttataaa cggatttcat accgctcaag gagacaagaa ctccaggaag       660
caaatccgtg ggttcttgaa gtacttcggg ggtagctttt tatggagctt cttccagtgg       720
ttctacaccg gcggcgacgt ttgtgggttc attcagttcc ctacttttgg tctgaaggcc       780
tggaagcaga cgttcttctt tgactttagc ctgacataca tcggtgccgg gatgatctgc       840
ccacatatag taaatatctc caccctcttg ggtgcaattc tttcttatgg gatattgtgg       900
ccactcatca gtaagaacaa gggtgactgg taccctgcag atgtcaaaga agcagcatg       960 aaaagtttgt acggttacaa ggccttcata tgcatcgctc tgatcatggg ggatggactc      1020
taccacttca ccaaaattat accgtcgac tgcaagggca tgtatcgaca gttcagccgt      1080
aaacatgctg acaaccgaga gaaaaatgtg acaatacag tctcactcga ggatttgcag      1140
cgcgacgtca cttcaagag gggccatctc cccgcttgga tcgcgtacag tgggtatgcc      1200
gtgctgagcg tcgttgcagt ggttaccacg ccaataatgt tccgacaagt gaaatggtac      1260
tacgtagtta tagcctatgt cgtcgccccc atgcttggat cgccaattc ctacgggacg      1320 gggctcaccg acatcaacat gggctataac tatggcaaga tagggctctt cgtcttcgcg      1380
ggttgggctg gcagggacaa tggtgtcgtt gcaggtctgg ttgttggtac atgtgtgaag      1440
cagctggtgc tgatatctgc agatttgatg caagacttca agacgagtta tctcactaag      1500
acatcaccaa gatccatgat ggtggcacag gcaattggga cagccatggg ctgcgttgtc      1560
tctccccttA cgttcatgct cttctacagg gcatttgata ttggcaatcc agatggtacc      1620
tggaaggcac cgtatgcact gatataccgt aatatggcaa tactcggtgt ggagggcttc      1680
```

-continued

```
tcagtactgc ccaagtattg cctggcactc tctggtggat ttttcgcgtt tgcagcaatc    1740
ctcagcatag caagagattt cacgccgcat aggtataggc agtatgtgcc cctgccaatg    1800
gcgatggcgg ttccattcct tgtcggcggg agctttgcga ttgatatgtg tgtcgggagt    1860
ttggtggttt ttatctggaa caagataaac aagaaggagg ccggcttcat ggtccctgca    1920
gttgcatccg gtttgatatg tggggatggg atatggacat tcccttcgtc catacttgct    1980
cttgccaaga ttacaccacc aatttgcatg aagtttacac ctgcacccta g             2031
```

<210> SEQ ID NO 4
<211> LENGTH: 51
<212> TYPE: DNA
<213> ORGANISM: Avena sativa

<400> SEQUENCE: 4

```
ttcagccgta aacatgctga caaccgagag aaaaatgtgg acaatacagt c              51
```

<210> SEQ ID NO 5
<211> LENGTH: 676
<212> TYPE: PRT
<213> ORGANISM: Avena sativa

<400> SEQUENCE: 5

```
Met Asp Val Leu Gly Pro Asp Arg Thr Arg Ile Ala Pro Glu Ile Glu
1               5                   10                  15

Lys His Val Ala Ala Glu Gly Asp Arg Glu Ser Asp Pro Ala Leu Ala
            20                  25                  30

Ala Glu Arg Glu Leu Glu Pro Leu Gly Arg Trp Gln Asp Glu Leu Thr
        35                  40                  45

Val Arg Gly Met Val Ala Ala Leu Leu Ile Gly Phe Ile Tyr Thr Val
    50                  55                  60

Ile Val Met Lys Ile Ala Leu Thr Thr Gly Leu Val Pro Thr Leu Asn
65                  70                  75                  80

Val Ser Ala Ala Leu Leu Ser Phe Leu Ala Leu Arg Gly Trp Thr Arg
                85                  90                  95

Leu Leu Asp Arg Phe Gly Ile Val Ser Arg Pro Phe Thr Arg Gln Glu
            100                 105                 110

Asn Thr Ile Val Gln Thr Cys Gly Val Ala Cys Tyr Thr Ile Ala Phe
        115                 120                 125

Ala Gly Gly Phe Gly Ser Thr Leu Leu Gly Leu Asn Lys Asn Thr Tyr
    130                 135                 140

Glu Leu Ala Gly Asp Ser Pro Gly Asn Gly Pro Gly Ser Tyr Lys Glu
145                 150                 155                 160

Pro Gly Ile Gly Trp Met Thr Ala Phe Leu Phe Ser Cys Ser Phe Gly
                165                 170                 175

Gly Leu Leu Thr Leu Ile Pro Leu Arg Gln Val Leu Val Val Asp Tyr
            180                 185                 190

Arg Leu Val Tyr Pro Ser Gly Thr Ala Thr Ala Val Leu Ile Asn Gly
        195                 200                 205

Phe His Thr Ala Gln Gly Asp Lys Asn Ser Arg Lys Gln Ile Arg Gly
    210                 215                 220

Phe Leu Lys Tyr Phe Gly Gly Ser Phe Leu Trp Ser Phe Phe Gln Trp
225                 230                 235                 240

Phe Tyr Thr Gly Gly Asp Val Cys Gly Phe Ile Gln Phe Pro Thr Phe
                245                 250                 255

Gly Leu Lys Ala Trp Lys Gln Thr Phe Phe Phe Asp Phe Ser Leu Thr
```

```
              260                 265                 270
Tyr Ile Gly Ala Gly Met Ile Cys Pro His Ile Val Asn Ile Ser Thr
            275                 280                 285
Leu Leu Gly Ala Ile Leu Ser Tyr Gly Ile Leu Trp Pro Leu Ile Ser
            290                 295                 300
Lys Asn Lys Gly Asp Trp Tyr Pro Ala Asp Val Lys Glu Ser Ser Met
305                 310                 315                 320
Lys Ser Leu Tyr Gly Tyr Lys Ala Phe Ile Cys Ile Ala Leu Ile Met
                325                 330                 335
Gly Asp Gly Leu Tyr His Phe Thr Lys Ile Ile Thr Val Asp Cys Lys
            340                 345                 350
Gly Met Tyr Arg Gln Phe Ser Arg Lys His Ala Asp Asn Arg Glu Lys
            355                 360                 365
Asn Val Asp Asn Thr Val Ser Leu Glu Asp Leu Gln Arg Asp Val Asp
            370                 375                 380
Phe Lys Arg Gly His Leu Pro Ala Trp Ile Ala Tyr Ser Gly Tyr Ala
385                 390                 395                 400
Val Leu Ser Val Val Ala Val Thr Thr Pro Ile Met Phe Arg Gln
                405                 410                 415
Val Lys Trp Tyr Tyr Val Val Ile Ala Tyr Val Val Ala Pro Met Leu
                420                 425                 430
Gly Phe Ala Asn Ser Tyr Gly Thr Gly Leu Thr Asp Ile Asn Met Gly
            435                 440                 445
Tyr Asn Tyr Gly Lys Ile Gly Leu Phe Val Phe Ala Gly Trp Ala Gly
            450                 455                 460
Arg Asp Asn Gly Val Val Ala Gly Leu Val Val Gly Thr Cys Val Lys
465                 470                 475                 480
Gln Leu Val Leu Ile Ser Ala Asp Leu Met Gln Asp Phe Lys Thr Ser
                485                 490                 495
Tyr Leu Thr Lys Thr Ser Pro Arg Ser Met Met Val Ala Gln Ala Ile
                500                 505                 510
Gly Thr Ala Met Gly Cys Val Val Ser Pro Leu Thr Phe Met Leu Phe
            515                 520                 525
Tyr Arg Ala Phe Asp Ile Gly Asn Pro Asp Gly Thr Trp Lys Ala Pro
            530                 535                 540
Tyr Ala Leu Ile Tyr Arg Asn Met Ala Ile Leu Gly Val Glu Gly Phe
545                 550                 555                 560
Ser Val Leu Pro Lys Tyr Cys Leu Ala Leu Ser Gly Gly Phe Phe Ala
                565                 570                 575
Phe Ala Ala Ile Leu Ser Ile Ala Arg Asp Phe Thr Pro His Arg Tyr
            580                 585                 590
Arg Gln Tyr Val Pro Leu Pro Met Ala Met Ala Val Pro Phe Leu Val
            595                 600                 605
Gly Gly Ser Phe Ala Ile Asp Met Cys Val Gly Ser Leu Val Val Phe
            610                 615                 620
Ile Trp Asn Lys Ile Asn Lys Lys Glu Ala Gly Phe Met Val Pro Ala
625                 630                 635                 640
Val Ala Ser Gly Leu Ile Cys Gly Asp Gly Ile Trp Thr Phe Pro Ser
                645                 650                 655
Ser Ile Leu Ala Leu Ala Lys Ile Thr Pro Pro Ile Cys Met Lys Phe
                660                 665                 670
Thr Pro Ala Pro
            675
```

<210> SEQ ID NO 6
<211> LENGTH: 17
<212> TYPE: PRT
<213> ORGANISM: Avena sativa

<400> SEQUENCE: 6

Phe Ser Arg Lys His Ala Asp Asn Arg Glu Lys Asn Val Asp Asn Thr
1               5                   10                  15

Val

<210> SEQ ID NO 7
<211> LENGTH: 2133
<212> TYPE: DNA
<213> ORGANISM: Avena sativa

<400> SEQUENCE: 7

| | | | | | |
|---|---|---|---|---|---|
| atggacgtcc | tgggccctga | ccgcacgcgg | atcgcgccgg | agatcgagaa | gcacgtggcc | 60 |
| gcggagggcg | acagggagtc | tgacccggcg | ctggccgcgg | agcgggagct | agagcccctg | 120 |
| ggcggtggc | aggacgagct | gaccgtgcgg | ggcatggtgg | cggcgctgct | catcgggttc | 180 |
| atctacaccg | tcatcgtcat | gaagatcgcg | ctcaccaccg | gctggtgcc | caccctcaac | 240 |
| gtctccgccg | cgctgctctc | cttcctcgcg | ctccgcggct | ggacgcgctt | gctggaccgc | 300 |
| ttcggcatcg | tgtcccgtcc | cttcacgcgg | caggagaaca | ccatcgtcca | gacctgcggc | 360 |
| gtcgcctgct | acaccatcgc | gttcgccggt | ggcttcgggt | caaccttgct | gggtctaaac | 420 |
| aagaacacgt | acgagctggc | cggcgactcg | ccgggcaacg | gccggggag | ctacaaggag | 480 |
| ccagggattg | gctggatgac | ggcattcctc | ttttcttgca | gcttcggggg | gctcctcacc | 540 |
| ttgattcccc | ttagacaggt | attggtcgtg | gactatagat | tagtgtaccc | aagtgggacg | 600 |
| gcaactgctg | ttcttataaa | cggatttcat | accgctcaag | gagacaagaa | ctccaggaag | 660 |
| caaatccgtg | ggttcttgaa | gtacttcggg | ggtagctttt | tatggagctt | cttccagtgg | 720 |
| ttctacaccg | gcggcgacgt | ttgtgggttc | attcagttcc | ctactttgg | tctgaaggcc | 780 |
| tggaagcaga | cgttcttctt | tgactttagc | ctgacataca | tcggtgccgg | gatgatctgc | 840 |
| ccacatatag | taaatatctc | caccctcttg | ggtgcaattc | tttcttatgg | gatattgtgg | 900 |
| ccactcatca | gtaagaacaa | gggtgactgg | taccctgcag | atgtcaaaga | agcagcatg | 960 |
| aaaagtttgt | acggttacaa | ggccttcata | tgcatcgctc | tgatcatggg | ggatggactc | 1020 |
| taccacttca | ccaaaattat | taccgtcgac | tgcaagggca | tgtatcgaca | gttcagccgt | 1080 |
| aaacatgctg | acaaccgaga | gaaaaatgtg | acaatacag | tctcactcga | ggatttgcag | 1140 |
| cgcgacgtcg | actgcaaggg | catgtatcga | cagttcagcc | gtaaacatgc | tgacaaccga | 1200 |
| gagaaaaatg | tggacaatac | agtctcactc | gaggatttgc | agcgcgacgt | cgacttcaag | 1260 |
| agggccatc | tccccgcttg | gatcgcgtac | agtgggtatg | ccgtgctgag | cgtcgttgca | 1320 |
| gtggttacca | cgccaataat | gttccgacaa | gtgaaatggt | actacgtagt | tatagcctat | 1380 |
| gtcgtcgccc | ccatgcttgg | attcgccaat | cctacgggga | cggggctcac | cgacatcaac | 1440 |
| atgggctata | actatggcaa | gatagggctc | ttcgtcttcg | cggttgggc | tggcagggac | 1500 |
| aatggtgtcg | ttgcaggtct | ggttgttggt | acatgtgtga | agcagctggt | gctgatatct | 1560 |
| gcagatttga | tgcaagactt | caagacgagt | atctcactga | agacatcacc | aagatccatg | 1620 |
| atggtggcac | aggcaattgg | gacagccatg | ggctgcgttg | tctctccccct | tacgttcatg | 1680 |
| ctcttctaca | gggcatttga | tattggcaat | ccagatggta | cctggaaggc | accgtatgca | 1740 |

```
ctgatatacc gtaatatggc aatactcggt gtggagggct tctcagtact gcccaagtat    1800
tgcctggcac tctctggtgg attttttcgcg tttgcagcaa tcctcagcat agcaagagat    1860
```
```
ctgatatacc gtaatatggc aatactcggt gtggagggct tctcagtact gcccaagtat    1800
tgcctggcac tctctggtgg attttttcgcg tttgcagcaa tcctcagcat agcaagagat    1860
ttcacgccgc ataggtatag gcagtatgtg ccctgccaa tggcgatggc ggttccattc    1920
cttgtcggcg ggagctttgc gattgatatg tgtgtcggga gtttggtggt ttttatctgg    1980
aacaagataa acaagaagga ggccggcttc atggtccctg cagttgcatc cggtttgata    2040
tgtggggatg ggatatggac attcccttcg tccatacttg ctcttgccaa gattacacca    2100
ccaatttgca tgaagtttac acctgcaccc tag                                 2133
```

<210> SEQ ID NO 8
<211> LENGTH: 710
<212> TYPE: PRT
<213> ORGANISM: Avena sativa

<400> SEQUENCE: 8

```
Met Asp Val Leu Gly Pro Asp Arg Thr Arg Ile Ala Pro Glu Ile Glu
1               5                   10                  15

Lys His Val Ala Ala Glu Gly Asp Arg Glu Ser Asp Pro Ala Leu Ala
            20                  25                  30

Ala Glu Arg Glu Leu Glu Pro Leu Gly Arg Trp Gln Asp Glu Leu Thr
        35                  40                  45

Val Arg Gly Met Val Ala Ala Leu Leu Ile Gly Phe Ile Tyr Thr Val
    50                  55                  60

Ile Val Met Lys Ile Ala Leu Thr Thr Gly Leu Val Pro Thr Leu Asn
65                  70                  75                  80

Val Ser Ala Ala Leu Leu Ser Phe Leu Ala Leu Arg Gly Trp Thr Arg
                85                  90                  95

Leu Leu Asp Arg Phe Gly Ile Val Ser Arg Pro Phe Thr Arg Gln Glu
            100                 105                 110

Asn Thr Ile Val Gln Thr Cys Gly Val Ala Cys Tyr Thr Ile Ala Phe
        115                 120                 125

Ala Gly Gly Phe Gly Ser Thr Leu Leu Gly Leu Asn Lys Asn Thr Tyr
    130                 135                 140

Glu Leu Ala Gly Asp Ser Pro Gly Asn Gly Pro Gly Ser Tyr Lys Glu
145                 150                 155                 160

Pro Gly Ile Gly Trp Met Thr Ala Phe Leu Phe Ser Cys Ser Phe Gly
                165                 170                 175

Gly Leu Leu Thr Leu Ile Pro Leu Arg Gln Val Leu Val Asp Tyr
            180                 185                 190

Arg Leu Val Tyr Pro Ser Gly Thr Ala Thr Ala Val Leu Ile Asn Gly
            195                 200                 205

Phe His Thr Ala Gln Gly Asp Lys Asn Ser Arg Lys Gln Ile Arg Gly
        210                 215                 220

Phe Leu Lys Tyr Phe Gly Gly Ser Phe Leu Trp Ser Phe Phe Gln Trp
225                 230                 235                 240

Phe Tyr Thr Gly Gly Asp Val Cys Gly Phe Ile Gln Phe Pro Thr Phe
                245                 250                 255

Gly Leu Lys Ala Trp Lys Gln Thr Phe Phe Asp Phe Ser Leu Thr
            260                 265                 270

Tyr Ile Gly Ala Gly Met Ile Cys Pro His Ile Val Asn Ile Ser Thr
        275                 280                 285

Leu Leu Gly Ala Ile Leu Ser Tyr Gly Ile Leu Trp Pro Leu Ile Ser
    290                 295                 300
```

```
Lys Asn Lys Gly Asp Trp Tyr Pro Ala Asp Val Lys Glu Ser Ser Met
305                 310                 315                 320

Lys Ser Leu Tyr Gly Tyr Lys Ala Phe Ile Cys Ile Ala Leu Ile Met
            325                 330                 335

Gly Asp Gly Leu Tyr His Phe Thr Lys Ile Ile Thr Val Asp Cys Lys
            340                 345                 350

Gly Met Tyr Arg Gln Phe Ser Arg Lys His Ala Asp Asn Arg Glu Lys
            355                 360                 365

Asn Val Asp Asn Thr Val Ser Leu Glu Asp Leu Gln Arg Asp Val Asp
            370                 375                 380

Cys Lys Gly Met Tyr Arg Gln Phe Ser Arg Lys His Ala Asp Asn Arg
385                 390                 395                 400

Glu Lys Asn Val Asp Asn Thr Val Ser Leu Glu Asp Leu Gln Arg Asp
                405                 410                 415

Val Asp Phe Lys Arg Gly His Leu Pro Ala Trp Ile Ala Tyr Ser Gly
                420                 425                 430

Tyr Ala Val Leu Ser Val Val Ala Val Val Thr Thr Pro Ile Met Phe
            435                 440                 445

Arg Gln Val Lys Trp Tyr Tyr Val Val Ile Ala Tyr Val Val Ala Pro
            450                 455                 460

Met Leu Gly Phe Ala Asn Ser Tyr Gly Thr Gly Leu Thr Asp Ile Asn
465                 470                 475                 480

Met Gly Tyr Asn Tyr Gly Lys Ile Gly Leu Phe Val Phe Ala Gly Trp
                485                 490                 495

Ala Gly Arg Asp Asn Gly Val Val Ala Gly Leu Val Val Gly Thr Cys
                500                 505                 510

Val Lys Gln Leu Val Leu Ile Ser Ala Asp Leu Met Gln Asp Phe Lys
            515                 520                 525

Thr Ser Tyr Leu Thr Lys Thr Ser Pro Arg Ser Met Met Val Ala Gln
            530                 535                 540

Ala Ile Gly Thr Ala Met Gly Cys Val Val Ser Pro Leu Thr Phe Met
545                 550                 555                 560

Leu Phe Tyr Arg Ala Phe Asp Ile Gly Asn Pro Asp Gly Thr Trp Lys
                565                 570                 575

Ala Pro Tyr Ala Leu Ile Tyr Arg Asn Met Ala Ile Leu Gly Val Glu
                580                 585                 590

Gly Phe Ser Val Leu Pro Lys Tyr Cys Leu Ala Leu Ser Gly Gly Phe
            595                 600                 605

Phe Ala Phe Ala Ala Ile Leu Ser Ile Ala Arg Asp Phe Thr Pro His
            610                 615                 620

Arg Tyr Arg Gln Tyr Val Pro Leu Pro Met Ala Met Ala Val Pro Phe
625                 630                 635                 640

Leu Val Gly Gly Ser Phe Ala Ile Asp Met Cys Val Gly Ser Leu Val
                645                 650                 655

Val Phe Ile Trp Asn Lys Ile Asn Lys Lys Glu Ala Gly Phe Met Val
                660                 665                 670

Pro Ala Val Ala Ser Gly Leu Ile Cys Gly Asp Gly Ile Trp Thr Phe
            675                 680                 685

Pro Ser Ser Ile Leu Ala Leu Ala Lys Ile Thr Pro Pro Ile Cys Met
            690                 695                 700

Lys Phe Thr Pro Ala Pro
705                 710
```

```
<210> SEQ ID NO 9
<211> LENGTH: 36
<212> TYPE: PRT
<213> ORGANISM: Avena sativa

<400> SEQUENCE: 9

Val Asp Cys Lys Gly Met Tyr Arg Gln Phe Ser Arg Lys His Ala Asp
1               5                   10                  15

Asn Arg Glu Lys Asn Val Asp Asn Thr Val Ser Leu Glu Asp Leu Gln
            20                  25                  30

Arg Asp Val Asp
        35
```